United States Patent
Rowlett

(10) Patent No.: US 12,233,070 B2
(45) Date of Patent: Feb. 25, 2025

(54) METHODS FOR TREATING BENZODIAZEPINE MISUSE/USE DISORDER

(71) Applicant: University of Mississippi Medical Center, Jackson, MS (US)

(72) Inventor: James K. Rowlett, Ridgeland, MS (US)

(73) Assignee: UNIVERSITY OF MISSISSIPPI MEDICAL CENTER, Jackson, MS (US)

(*) Notice: Subject to any disclaimer, the term of this patent is extended or adjusted under 35 U.S.C. 154(b) by 0 days.

(21) Appl. No.: 17/361,754

(22) Filed: Jun. 29, 2021

(65) Prior Publication Data

US 2021/0401849 A1    Dec. 30, 2021

Related U.S. Application Data

(60) Provisional application No. 63/046,615, filed on Jun. 30, 2020.

(51) Int. Cl.
*A61P 25/30* (2006.01)
*A61K 31/501* (2006.01)
*A61K 31/5025* (2006.01)
*A61K 31/53* (2006.01)

(52) U.S. Cl.
CPC ............ *A61K 31/53* (2013.01); *A61K 31/501* (2013.01); *A61K 31/5025* (2013.01); *A61P 25/30* (2018.01)

(58) Field of Classification Search
CPC .................................. A61K 31/53; A61P 25/30
See application file for complete search history.

(56) References Cited

U.S. PATENT DOCUMENTS

| | | |
|---|---|---|
| 2008/0255097 A1 | 10/2008 | Sabnani et al. |
| 2011/0009441 A1 | 1/2011 | Trabanco-Suarez et al. |
| 2016/0213680 A1 | 7/2016 | Hassan et al. |
| 2019/0134057 A1* | 5/2019 | Zeilhofer ............. A61K 31/437 |

FOREIGN PATENT DOCUMENTS

| | | |
|---|---|---|
| WO | 2011/011712 A1 | 1/2011 |
| WO | 2019/204446 A1 | 10/2019 |

OTHER PUBLICATIONS

Lalive et al. ("Is there a way to curb benzodiazepine addiction?" Swiss Medical Weekly • Review article: Current opinion. (Oct. 9, 2011);141:w13277. doi:10.4414/smw.2011.13277) . (Year: 2011).*
Kohut et al. ("Novel Discriminative Stimulus Effects of TPA023B, Subtype-Selective γ-aminobutyric-acidA/Benzodiazepine Modulator: Comparisons with Zolpidem, Lorazepam, and TPA023." Pharmacol Biochem Behav. Jul. 2008; 90(1): 65-73. Published online Feb. 26, 2008. doi: 10.1016/j.pbb.2008.02.019.) (Year: 2008).*
International Preliminary Report on Patentability received for PCT Patent Application No. PCT/US2021/039920, mailed on Jan. 12, 2023, 7 pages.
International Search Report and Written Opinion received for PCT Patent Application No. PCT/US21/39920, mailed on Dec. 8, 2021, 11 pages.
Russell et al., "Discovery of Imidazo[1,2-b][1,2,4]triazines as GABAA a2/3 Subtype Selective Agonists for the Treatment of Anxiety", J. Med. Chem., 2006, vol. 49, pp. 1235-1238.
Saxon et al., "Effects of flumazenil in the treatment of benzodiazepine withdrawal—a double-blind pilot study", Psychopharmacology, 1997, vol. 131, pp. 153-160.
Shinday et al., "Reinforcing Effects Of Compounds Lacking Intrinsic Efficacy at a I Subunit-Containing GABAA Receptor Subtypes in Midazolam—But Not Cocaine-Experienced Rhesus Monkeys", Neuropsychopharmacology, 2013, vol. 38, pp. 1006-1014.
Supplementary European Search Report received for EP Patent Application No. 21834525.4, mailed on Jun. 14, 2024, 20 pages.

* cited by examiner

*Primary Examiner* — Jeffrey S Lundgren
*Assistant Examiner* — Chris E Simmons
(74) *Attorney, Agent, or Firm* — Workman Nydegger

(57) ABSTRACT

Disclosed are compositions and methods for treating benzodiazepine misuse and/or use disorder. A method of treating benzodiazepine misuse and/or use disorder includes administering to a subject in need thereof of an effective amount of a compound provides both partial modulator and antagonist effects at $GABA_A$ receptors.

16 Claims, 11 Drawing Sheets

METHODS FOR TREATING BENZODIAZEPINE MISUSE/USE DISORDER

CROSS-REFERENCE TO RELATED APPLICATIONS

This application claims the benefit of and priority to U.S. Provisional Patent Application Ser. No. 63/046,615, filed Jun. 30, 2020, the entirety of which is incorporated herein by this reference.

STATEMENT REGARDING FEDERALLY SPONSORED RESEARCH

This invention was made with government support under grant no. DA011792 awarded by the National Institute on Drug Abuse. The government has certain rights in the invention.

BACKGROUND

Technical Field

This disclosure relates to compositions for use in treating benzodiazepine misuse and/or use disorder and related methods of using such compounds for treating benzodiazepine misuse and/or use disorder.

Related Technology

Benzodiazepines were originally developed as anxiety-reducing ("anxiolytic") and sedative drugs for treating anxiety and sleep disorders. Commonly prescribed benzodiazepines include diazepam (trade name: Valium®), alprazolam (trade name: Xanax®), clonazepam (trade name: Klonopin®), lorazepam (trade name: Ativan®), midazolam (trade name: Versed®), and temazepam (trade name: Restoril®). The core of a benzodiazepine is a fusion of a benzene ring and a diazepine ring, with a sometimes-substituted phenyl group attached to the diazepine.

Since their introduction in the 1960's, benzodiazepines have been associated with liability for abuse and dependence. Benzodiazepine abuse can be characterized as "misuse" (use outside of prescription directions) and "use disorder" (as defined by WHO guidelines, a mental disorder in which benzodiazepine consumption is uncontrolled and detrimental to psychosocial functioning, usually accompanied by physical dependence).

Recent epidemiological findings suggest that the abuse of benzodiazepines may be on the rise, with misuse among U.S. adults accounting for nearly 20% of substance use overall. Benzodiazepine prescription rates remain relatively high in the U.S. (~8% of the population), with females prescribed at rates approximately 3-fold higher than men across all age groups. U.S. treatment admissions due to benzodiazepine use increased 43% from 2006 to 2016. Of particular concern is the increase in overdose deaths caused by benzodiazepines combined with opioids. Moreover, in concert with the COVID-19 pandemic, anti-anxiety prescriptions in the U.S. increased 34.1% from mid-February to mid-March in 2020.

Despite these issues, no approved and broadly effective pharmacotherapy exists for the treatment of benzodiazepine misuse and/or use disorder. Current options are off-label use of other benzodiazepines, gabapentin (a drug used for neuralgia treatment), or sodium phenobarbital (an anesthetic barbiturate). These treatment options have minimal supportive evidence of efficacy in treating benzodiazepine misuse and/or use disorder. Moreover, use of barbiturates such as sodium phenobarbital is concerning given the toxicity and abuse liability of such drugs.

Accordingly, there is an ongoing need for improved therapies for treating benzodiazepine misuse and/or use disorder. Such therapies should ideally be capable of effectively suppressing the effects of conventional benzodiazepines without themselves introducing increased abuse potential. Such therapies should also ideally provide such effects without introducing significant motor coordination deficits, appetite suppression, respiratory suppression, or other unwanted physiological side effects. Such therapies should also ideally provide such effects without precipitating benzodiazepine withdrawal.

SUMMARY

This disclosure is directed to compositions and methods for treating benzodiazepine misuse and/or use disorder. Compounds disclosed herein have mixed partial modulator and antagonist profiles. These partial modulator/antagonist compounds have reduced abuse potential relative to benzodiazepines yet retain the ability to reduce anxiety. Compounds disclosed herein are capable of blocking the effects of benzodiazepines directly (i.e., independent of sedative or motor effects of the compound). Compounds disclosed herein have not demonstrated the ability to precipitate withdrawal following bolus doses of benzodiazepines, suggesting an exceptional ease-of-transition to treatment.

In one embodiment, a method of treating benzodiazepine misuse and/or use disorder comprises administering to a subject in need thereof of an effective amount of a compound that provides both partial modulator and antagonist effects at $GABA_A$ receptors. The compound may be a compound of Formula I, Formula II, Formula III (as those Formulas are described in more detail below), or a combination or mixture thereof.

In some embodiments, the treatment provides an anxiolytic effect, but wherein positive reinforcing effects of the compound are less than from a conventional benzodiazepine. In some embodiments, the compound functions to suppress the effects of a conventional benzodiazepine independent of sedative effects or motor effects of the administered partial modulator/antagonist compound. In some embodiments, the suppression is insurmountable and thus cannot be negated by increased benzodiazepine dosing.

In some embodiments, the compound is administered at a dose of greater than or equal to about 0.01 mg/kg or greater than about 0.03 mg/kg. In some embodiments, the treatment provides both anxiolytic and benzodiazepine suppression effects when administered.

In some embodiments, the treatment does not induce substantial motor coordination deficits in the subject, does not induce substantial appetite suppression in the subject, and does not substantially affect breathing frequency, tidal volume, or minute volume in the subject.

In some embodiments, the treatment does not precipitate benzodiazepine withdrawal. For example, the compound may be administered without prior or concurrent detoxification treatment of the subject, or with less detoxification as compared to conventional treatment options.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

BRIEF DESCRIPTION OF THE DRAWINGS

Various objects, features, characteristics, and advantages of the invention will become apparent and more readily appreciated from the following description of the embodiments, taken in conjunction with the accompanying drawings and the appended claims, all of which form a part of this specification. In the Drawings, like reference numerals may be utilized to designate corresponding or similar parts in the various Figures, and the various elements depicted are not necessarily drawn to scale, wherein:

FIG. 7A: data as mean #injections/session+/−SEM. FIG. 7B: data as mean % maximum, obtained as maximal #injections/session for individual monkeys. Error bars are omitted from the bottom panel for clarity.

DETAILED DESCRIPTION

Overview of Benzodiazepines

Embodiments described herein are directed to compounds and methods for treating benzodiazepine misuse and/or use disorder. Benzodiazepines have the following general structure:

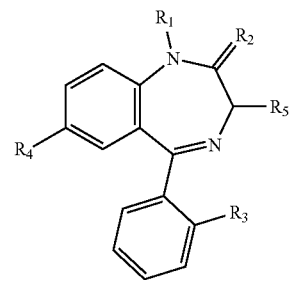

As shown, the core of a benzodiazepine is a fusion of a benzene ring and a diazepine ring, with an optionally substituted phenyl group attached to the diazepine. $R_1$ is typically H or $CH_3$; $R_2$ is typically O; or $R_1$ and $R_2$ together form an optionally substituted diazole or triazole ring fused to the diazepine ring. $R_3$ is typically Cl, F, or is absent. $R_4$ is typically Cl, F, or a nitro group. $R_5$ is typically an OH or is absent.

Other benzodiazepine-like drugs are not technically benzodiazepines but involve similar treatment targets and mechanisms of action and are therefore sometimes associated with benzodiazepines. For example, certain non-benzodiazepine hypnotics, often referred to as "Z-drugs" are structurally different from benzodiazepines but are similarly utilized to modulate the $GABA_A$ receptor and are also sometimes associated with misuse and/or use disorder. The Z-drugs include zopiclone, eszopiclone (trade name: Lunesta®), zaleplon (trade name: Sonata®), and zolpidem (trade name: Ambien®).

The compositions and methods described herein may be utilized to treat misuse and/or use disorder of benzodiazepines, Z-drugs, or both. For simplicity, the term "benzodiazepine(s)" will be used to refer to both conventional benzodiazepines (i.e., those compounds having a benzodiazepine structure as illustrated above) and benzodiazepine-like drugs such as Z-drugs. The term "conventional benzodiazepine(s)" will be used to specify compounds having a benzodiazepine structure.

Figure 1A:
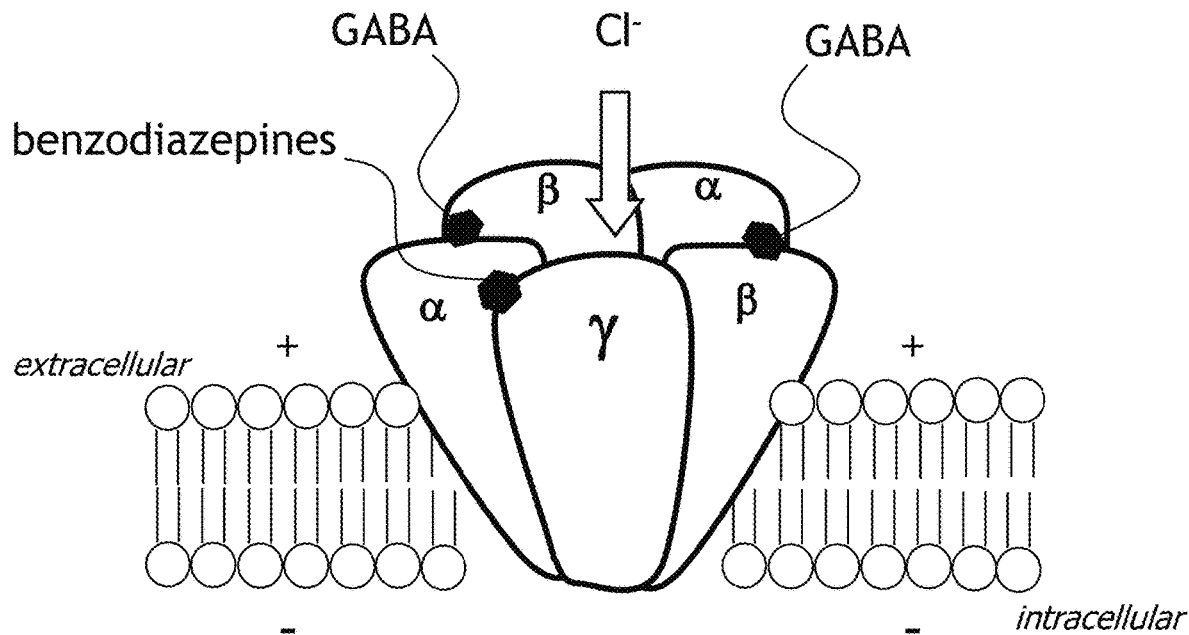
FIGS. 1A and 1B illustrate the $GABA_A$ receptor and its protein family subunits, showing allosteric binding to $GABA_A$ receptors and enhancement of the ability of GABA to increase chloride conductance.
Figure 1B:
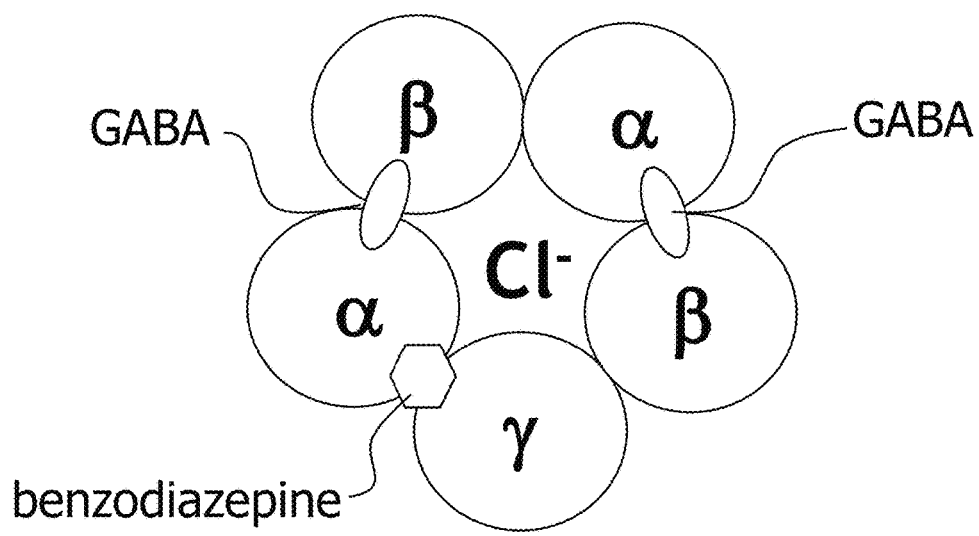

Benzodiazepines act by binding allosterically to $GABA_A$ receptors and enhancing the ability of GABA to increase chloride conductance. Benzodiazepines are therefore positive allosteric modulators of GABA. As illustrated in FIGS. 1A and 1B, $GABA_A$ receptors in the central nervous system are pentamers including structurally distinct proteins, with each protein family comprised of different subunits. The majority of $GABA_A$ receptors consist of α, β, and γ subunit families arranged in the sequence αβαβγ as viewed from "above" the synapse (FIG. 1B).

The effects of benzodiazepines appear to be determined predominantly by the presence of particular α subunits.

Benzodiazepine-type drugs bind to a site on the native $GABA_A$ receptor located at the interface of the γ2 subunit with either α1, α2, α3, or α5 subunits (i.e., $α1GABA_A$, $α2GABA_A$, $α3GABA_A$, $α5GABA_A$ subtypes; respectively), whereas most of these drugs are inactive at corresponding α4- and α6-subunit containing receptors (i.e., $α4GABA_A$, $α6GABA_A$ subtypes; respectively). Embodiments described herein primarily modulate the $GABA_A$ receptor via interactions with $α1GABA_A$, $α2GABA_A$ and $α3GABA_A$ receptor subtypes, which are believed to be important for mediating the abuse-related and anxiolytic effects of benzodiazepines.

Exemplary Partial Modulator/Antagonist Compounds

Compound design and discovery in the area of positive modulators of $GABA_A$ receptors have been hampered by difficulties in addressing selectivity for $α2GABA_A$ and $α3GABA_A$ subtypes (Atack 2011, *Current Topics in Med Chem,* 11: 1176-202; Maramai et al. 2020, *J Med Chem* 63: 3425-46). Little success has been achieved in identifying compounds with "selective affinity", i.e., different binding constants (potencies) for different subtypes. Instead, the approach that has emerged is "selective efficacy", in which intrinsic efficacy at subtypes or subtype combinations that represent targets range from full to partial modulation, whereas subtypes or subtype combinations that are associated with side effects have intrinsic efficacy ideally at zero (i.e., are antagonists at these sites). Assuming that antagonists have no functional effects, then behaviors engendered at the sites with >0 efficacy can be interpreted as mediated by those sites.

The concept of intermediate efficacy, or "partial agonism" has driven drug discovery based on the observation that lower levels of in vitro efficacy predict weaker behavioral effects. For allosteric modulators, the equivalent term is "partial modulator". Certain embodiments described herein beneficially function as subtype-selective partial modulators and as antagonists.

Table 1 lists a series of compounds developed originally by Merck & Co. that demonstrate no differences in receptor subtype affinity but act as partial positive modulators for particular subtype combinations while having zero efficacy (i.e., antagonism) at other subtypes. The chemistry and basic pharmacology of these compounds have been reviewed in the literature (reviewed by Atack 2011). Notably, however, prior research has not explored the potential use of such compounds for treating benzodiazepine misuse and/or use disorder.

TABLE 1

Compound series with activity at α1, α2, α3, and α5 subunit-containing $GABA_A$ receptors

| Chemical Series | Compound | Pharma-cokinetics*** | Subtype α1 | α2 | α3 | α5 |
|---|---|---|---|---|---|---|
| Imidazo-triazines | TPA023B | good | none | partial | partial | partial |
| | MRK-968 | good | none | partial | partial | none |
| | MRK-973 | good | none | partial | partial | partial |
| Imidazo-pyrimidines | MRK-623 | poor | none | partial | partial | none |
| | MRK-898 | good | none | partial | partial | none |
| Triazolo-pyridazines | MRK-696 | poor | partial | partial | partial | partial |
| | L-838,417* | poor | none | partial | partial | partial |
| | TPA023** | good | none | partial | partial | none |
| | MRK-409 | good | partial | partial | partial | partial |
| Pyridazines | MRK-257 | good | none | partial | partial | partial |
| | MRK-547 | good | none | partial | partial | none |
| | MRK-100 | good | none | none | partial | none |

*deuterated form developed by Concert Pharmaceuticals, out-licensed to Cipla Technologies.
**Halted in Phase II due to adverse effects (cataracts; Möhler 2011, *Neuropharmacology* 60: 1042-49), post hoc analysis revealed anxiolysis in patients with Generalized Anxiety Disorder.
***"poor" - low bioavailability and/or short half-life; "good" - potent with long half-life.

The imidazotriazine TPA023B was researched for its use as a non-sedating anxiolytic drug (Atack 2011). In Merck's preclinical programs, TPA023B was found to be minimally sedating (rodent rotarod and chain-pulling, squirrel monkey lever pressing) and to have anxiolytic-like effects (rodent elevated plus maze, conditioned suppression of drinking, fear-potentiated startle; squirrel monkey conditioned emotional response; Atack et al. 2010, J Psychopharmacol 25: 329-344). Using both in vivo occupancy and imaging studies, minimally-effective doses of TPA023B in anxiolysis assays in rodents and primates occurred at doses occupying 61-88% of CNS benzodiazepine binding sites (Atack et al. 2010).

In a Phase I Clinical Trial (Atack et al. 2010), TPA023B was orally-dosed in men up to 3.0 mg/70 kg. This dose engendered fatigue and drowsiness in some subjects (1-4 subjects out of 8 total). At a dose of 1.5 mg/70 kg, however, no adverse effects were obtained. This dose resulted in 50-55% occupancy of CNS benzodiazepine binding sites, as measured via PET. No ataxia was observed at any dose. These mild sedative effects are consistent with our findings in monkeys.

These prior investigations were focused on developing a non-sedating anxiolytic, and therefore did not discuss the investigated compounds in the context of treating benzodiazepine misuse and/or use disorder. While even a small degree of drowsiness might be considered (or may be considered detrimental) in the development of an anxiolytic, these effects likely are acceptable for applications in benzodiazepine misuse and/or use disorder. Moreover, these mild sedative effects are significantly less than typically observed with off-label pharmacotherapies used currently to treat this disorder, e.g., phenobarbital, gabapentin, or tapering with other conventional benzodiazepines.

Other unwanted side effects associated with benzodiazepine use are cognitive deficits, described clinically as anterograde amnesia. While relatively little data are available regarding the effects of selective efficacy compounds on cognitive function, a study by Soto et al. (2013, *Neuropsychopharmacology* 38: 2315-25) evaluated the effects of TPA023B on cognition in rhesus monkeys, in comparison with the conventional benzodiazepine triazolam. In a delayed matching-to-sample (DMTS) task of visual recognition memory and self-ordered spatial search (SOSS) task of spatial working memory, triazolam significantly reduced accuracy in both procedures, consistent with cognitive impairing effects reported with conventional benzodiazepines. In contrast, TPA023B did not alter accuracy or the number of trials completed in either task, suggesting that this compound lacks effects on visual/spatial memory.

In some embodiments, a compound for treating benzodiazepine misuse and/or use disorder is according to Formula I:

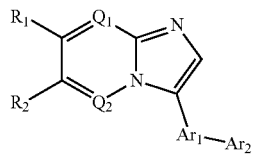

Formula I

In Formula I, $R_1$ and $R_2$ are independently H, Cl, F, $CF_3$, CN, alkyl (e.g., C1-C5), alkoxy (e.g., C1-C5), $OCF_3$, or an isopropanol group:

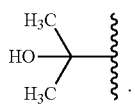

In certain preferred embodiments, one of $R_1$ and $R_2$ is H, and the other is $CH_3$, $CF_3$, or an isopropanol group. For example, in some embodiments, $R_1$ is $CH_3$, $CF_3$, or an isopropanol group and $R_2$ is H.

$Q_1$ and $Q_2$ are each independently C or N. In preferred embodiments, one or both of $Q_1$ or $Q_2$ are N, giving the compound an imidazopyrimidine or imidazotriazine core.

$Ar_1$ and $Ar_2$ are each 6-membered aromatic rings, each of which are optionally substituted with one or two substituents. Each of $Ar_1$ and $Ar_2$ may independently include one or more heteroatoms selected from 0 or N.

In some embodiments, $Ar_1$ and $Ar_2$ are each independently a phenyl, pyridine, pyridazine, pyrimidine, or pyrazine. In embodiments where one or both of $Ar_1$ or $Ar_2$ are substituted, the substituents comprise one or more of Cl, F, $CF_3$, CN, alkyl (e.g., C1-C5), alkoxy (e.g., C1-C5), or $OCF_3$. In preferred embodiments, the substituents are F and/or CN.

In some embodiments, $Ar_1$ and $Ar_2$ form a biphenyl group:

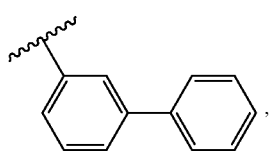 [SMILES: *c1cccc(-c2ccccc2)c1]

wherein one or both of the phenyl groups are optionally substituted F and/or CN.

In some embodiments, compounds of Formula I may be fully or partially deuterated.

Figure 2:
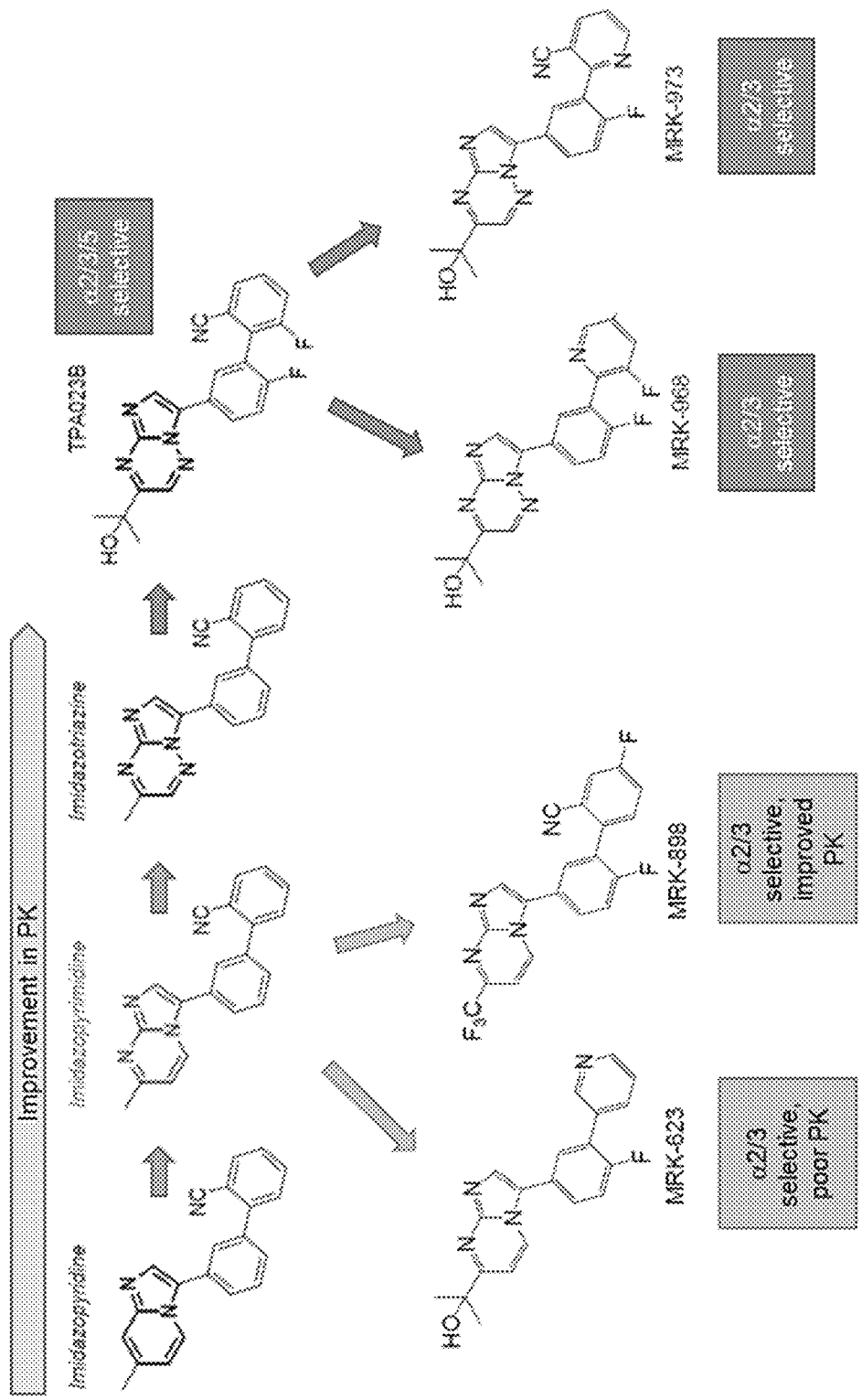
FIGS. 2 through 4 illustrate exemplary compounds according to Formulas I, II, and III, respectively, that may be utilized to treat benzodiazepine misuse and/or use disorder.

FIG. 2 illustrates a few exemplary compounds according to Formula I. Sequential addition of nitrogen atoms to the benzimidazole core of imidazopyridine enhances bioavailability and half-life without affecting binding and efficacy characteristics (Maramai et al., 2020), resulting in imidazopyrimidines and imidazotriazines as key analogues. TPA023B, a preferred compound for the embodiments described herein, is an imidazotriazine with a fluorinated biphenyl structure. MRK-968 and MRK-973 are notable variants of TPA023B. Analogues of the key intermediary, imidazopyrimidine, have improved plasma half-lives by fluorination, with MRK-898, for example, having effective half-life, bioavailability, and selectivity (rhesus monkey bioavailability of 49%, half-life of 13 h; antagonist at α1/α5GABAA subtypes; Atack, 2011). MRK-623 of this series has fair bioavailability but a very short half-life (0.5 h in rhesus monkey). However, a deuterated formulation of such compounds can improve half-life.

In some embodiments, a compound for treating benzodiazepine misuse and/or use disorder includes a triazolopyridazine core according to Formula II:

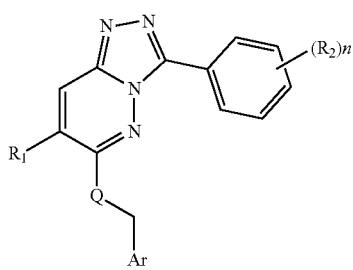

Formula II

In Formula II, $R_1$ is H, Cl, F, $CF_3$, CN, alkyl (e.g., C1-C5), or cycloalkyl (e.g., cyclopropyl, cyclobutyl, cyclopentyl). In some preferred embodiments, $R_1$ is isopropyl or cyclobutyl.

$R_2$ is H, Cl, F, $CF_3$, CN, alkyl (e.g., C1-C5), alkoxy (e.g., C1-C5), or $OCF_3$, and n is 1 or 2. In some preferred embodiments, $R_2$ is F.

Q is C, N, O, S, sulfone, or sulfoxide. In some preferred embodiments, Q is O.

Ar is an optionally substituted diazole, triazole, or pyridine. In some preferred embodiments, Ar is a substituted triazole:

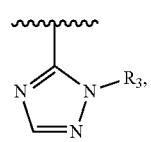

wherein $R_3$ is H or C1-C2 alkyl.

Figure 3:
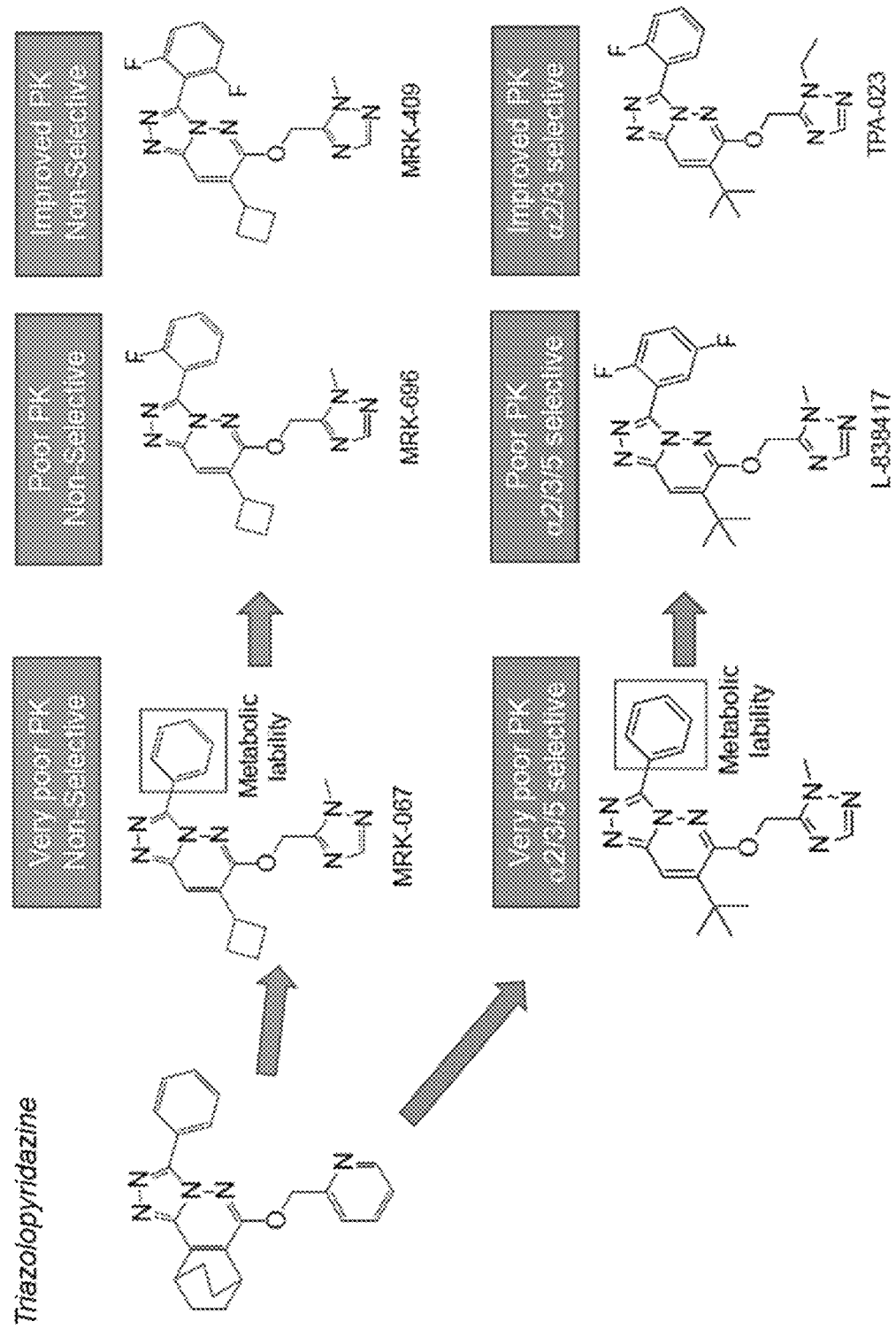

FIG. 3 illustrates a few exemplary compounds according to Formula II. The triazolopyridazines include TPA023, which was advanced to Phase II clinical trials but halted due to cataract development. Post hoc analyses showed significant anxiolysis in patients with Generalized Anxiety Disorder in three clinical trials (Atack 2009, *Adv Pharmacol* 57: 137-85). As shown, replacement of the bicyclic group of the starting triazolopyridazine molecule increases efficacy. The poor PK of MRK-067 is remedied by fluorination of the phenyl group. Replacement of the bicyclic group of triazolopyridazine with t-butyl substitutions provides L-838,417 and TPA023, both with no efficacy at $α1GABA_A$ subtypes. Poor PK has been addressed by the development of deuterated L-838,417 (also referred to as "C 21191" or "CTP-354").

In some embodiments, a compound for treating benzodiazepine misuse and/or use disorder includes a pyridazine core according to Formula III:

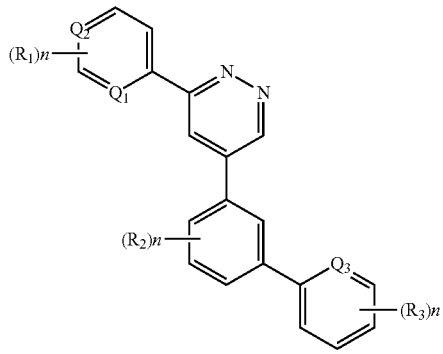

Formula III

In Formula III, each of $Q_1$, $Q_2$, and $Q_3$ are independently C or N. In some preferred embodiments, at least one of $Q_1$ or $Q_2$ is N and $Q_3$ is N.

Each $R_1$ (n is 1 or 2) is H, Cl, F, $CF_3$, CN, C1-C5 alkyl, C1-C5 alkoxy, or $OCF_3$. Likewise, each $R_2$ (n is 1 or 2) is H, Cl, F, $CF_3$, CN, C1-C5 alkyl, C1-C5 alkoxy, or $OCF_3$ and each $R_3$ (n is 1 or 2) is H, Cl, F, $CF_3$, CN, C1-C5 alkyl, C1-C5 alkoxy, or $OCF_3$. In some preferred embodiments, $R_1$, $R_2$, and $R_3$ are F.

Figure 4:
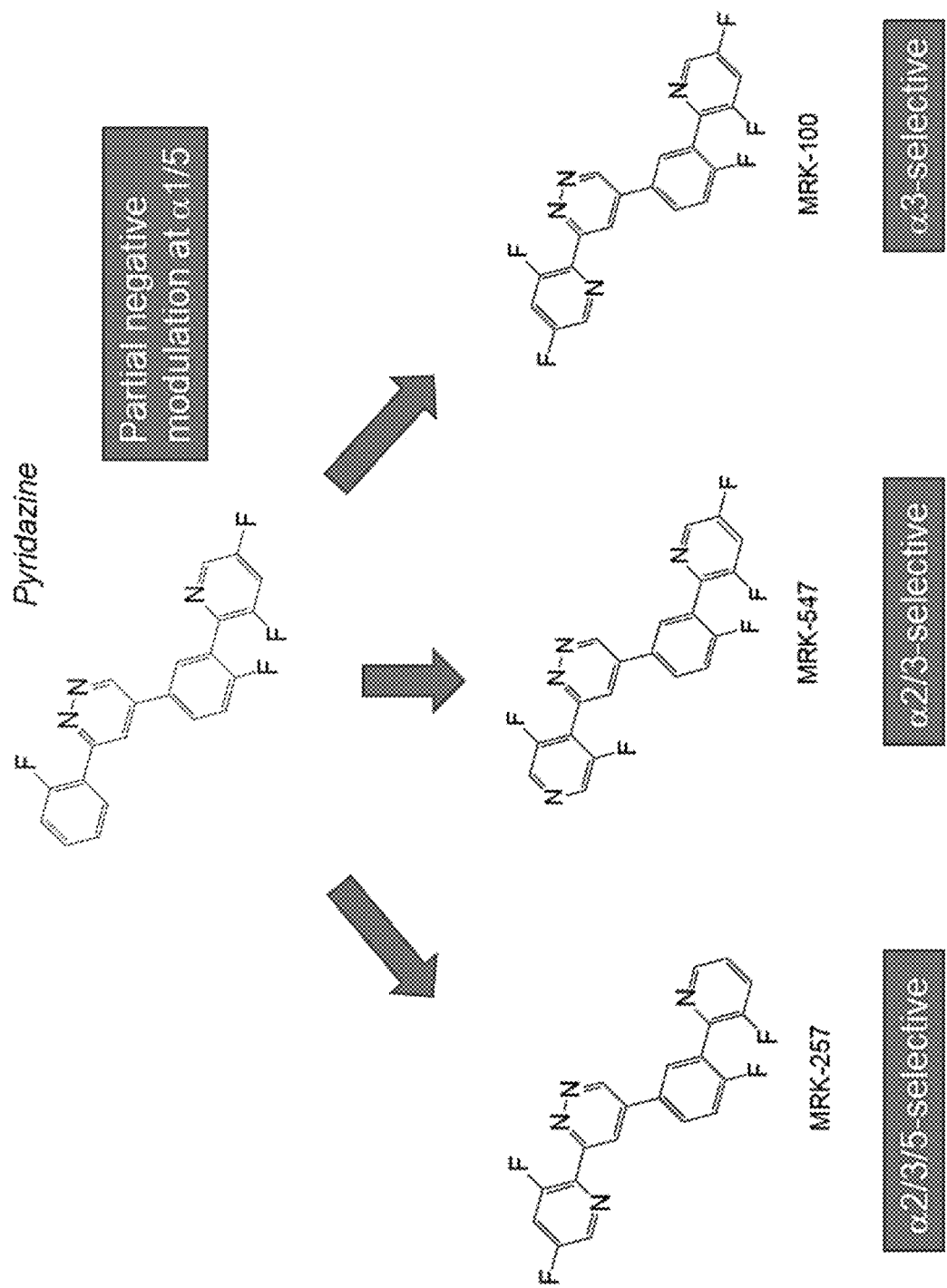

FIG. 4 illustrates a few exemplary compounds of Formula III. These compounds were originally developed as α5GABA$_A$-selective ligands, but instead had efficacy profiles as partial positive modulators with selectivity when fluorination approaches were used to address metabolic lability. Initial PK of all three compounds is relatively good, with the possible exception of MRK-547 in which in vitro results were not correlated with in vivo findings (Atack, 2011). The three compounds have differing selectivity, with MRK-100 showing α3GABA$_A$ partial modulation only. This is noteworthy because a compound with full positive modulation of α3GABA$_A$ receptors can have relatively low abuse potential (Meng et al. 2020; J Psychopharmacol 34: 348-357).

Treatment of Benzodiazepine Misuse and/or Use Disorder

The compounds described herein may be effectively utilized for treating benzodiazepine misuse and/or use disorder. An effective dose of such a compound, when administered to a subject in need thereof, beneficially provides an anxiolytic effect as a result of its partial modulator function, but with positive reinforcing effects less than those from benzodiazepines (including from "conventional benzodiazepines") so as not to transfer abuse of one compound to another.

The compounds described herein also beneficially provide antagonist effects and function to suppress the effects of benzodiazepines (including "conventional benzodiazepines"). As demonstrated herein, the suppressive effect is not merely a side effect of sedative and/or motor effects of the compound but is instead directly related to antagonism of the GABA$_A$ receptor. As further demonstrated herein, in at least some circumstances the suppression of benzodiazepine effects is insurmountable. That is, the suppression cannot be completely countered by simply increasing the dose of benzodiazepines.

In some embodiments, the compound is administered at a dose of about 0.005 mg/kg to about 10 mg/kg, or more preferably at a dose of about 0.01 mg/kg to about 1 mg/kg. For example, compounds described herein may be administered at doses of about 0.01, 0.02, 0.03, 0.05, 0.06, 0.07, 0.08, 0.09, 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, or 10.0 mg/kg, or within a dosage range with any two of the foregoing values as endpoints. Preferred dosages for humans may be about 0.5 mg/70 kg (0.007 mg/kg) to about 5.0 mg/70 kg (0.07 mg/kg), or about 1.0 mg/70 kg (0.01 mg/kg) to about 2.0 mg/70 kg (0.03 mg/kg). Higher doses are also possible but are not believed to be efficient use of the compound given that up to about 90-95% of benzodiazepine binding sites are occupied at doses as low as about 0.3 mg/kg to 1.0 mg/kg (e.g., 0.32 mg/kg i.v. provides 95% or greater occupancy in baboons; oral doses to Sprague Dawley rats provides 0.3 mg/kg=87%, 1.0 mg/kg=96%, and 3.0 mg/kg=99% occupancy).

Beneficially, compounds described herein are capable of providing both anxiolytic effects (as a result of partial modulator functionality) and benzodiazepine suppression effects (as a result of antagonist functionality) simultaneously. These effects enable the compounds to be effectively used to treat benzodiazepine misuse and/or use disorder.

As demonstrated herein, the beneficial effects of administration of the disclosed compounds are achievable without inducing substantial motor coordination deficits or appetite suppression in the subject. As further demonstrated herein, the beneficial effects are achievable without substantially affecting breathing frequency, tidal volume, or minute volume in the subject.

Moreover, compounds described herein enable partial modulator and antagonist effects without precipitating benzodiazepine withdrawal. This beneficially enables treatment of subjects that are physically dependent on benzodiazepines without the need for (or at least with significantly less need for) prior or concurrent detoxification treatment, which can be difficult and time-consuming.

Pharmaceutical Compositions

While it is possible for the compounds described herein to be administered alone, it may be preferable to formulate the compounds as pharmaceutical compositions (e.g., formulations). As such, in yet another aspect, pharmaceutical compositions useful in the methods and uses of the disclosed embodiments are provided. A pharmaceutical composition is any composition that may be administered in vitro or in vivo or both to a subject to treat, prevent, or ameliorate a condition or may otherwise be administered prophylactically to improve or maintain the health of the subject. In a preferred embodiment, a pharmaceutical composition may be administered in vivo. A subject will most often be a human, but this disclosure also covers situations where compounds are administered to mammals (e.g., as part of a testing protocol).

The compositions of the invention may be injectable suspensions, solutions, sprays, lyophilized powders, syrups, elixirs, and the like. Any suitable form of composition may be used. To prepare such a composition, a composition of the disclosure, having the desired degree of purity, is mixed with one or more pharmaceutically acceptable carriers and/or excipients.

As used herein the terms "pharmaceutically acceptable" and "physiologically acceptable" mean a biologically compatible formulation, gaseous, liquid, or solid, or mixture thereof, which is suitable for one or more routes of administration, in vivo delivery, or contact. A formulation is compatible where it does not induce adverse side effects that outweigh any prophylactic or therapeutic effect or benefit.

In an embodiment, the pharmaceutical compositions may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH and may range from a pH of about 3 to a pH of about 11, preferably about pH 3 to about pH 7, depending on the formulation and route of administration. In alternative embodiments, it may be preferred that the pH is adjusted to a range from about pH 5 to about pH 8. More particularly, the pharmaceutical compositions may comprise a therapeutically or prophylactically effective amount of at least one compound as described herein, together with one or more pharmaceutically acceptable excipients.

Formulations, for example, for parenteral or oral administration, are most typically solids, liquid solutions, emulsions, or suspensions, while inhalable formulations for intranasal or pulmonary administration are generally liquids or powders. An exemplary pharmaceutical composition may be formulated as a lyophilized solid that is reconstituted with a physiologically compatible solvent or carrier prior to administration. Other suitable carriers or diluents can be water or a buffered saline, with or without a preservative.

Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN® PLURONICS® or polyethylene glycol (PEG).

Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, and amino acid copolymers. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol, and ethanol; wetting or emulsifying agents; pH buffering substances; and the like. Liposomes are also included within the definition of pharmaceutically acceptable excipients.

For example, pharmaceutically acceptable excipients particularly suitable for use in conjunction with tablets include, for example, inert diluents, such as celluloses, calcium or sodium carbonate, lactose, calcium, or sodium phosphate; disintegrating agents, such as cross-linked povidone, maize starch, or alginic acid; binding agents, such as povidone, starch, gelatin, or acacia; and lubricating agents, such as magnesium stearate, stearic acid, or talc. Pharmaceutical compositions may also be formulated as dispersible powders and granules suitable for preparation of a suspension by the addition of suitable excipients.

As another example, pharmaceutical compositions may be formulated as suspensions comprising a compound as disclosed herein in admixture with at least one pharmaceutically acceptable excipient suitable for the manufacture of a suspension. Excipients suitable for use in connection with suspensions include suspending agents, such as sodium carboxymethylcellulose, methylcellulose, hydroxypropyl methylcellulose, sodium alginate, polyvinylpyrrolidone, gum tragacanth, gum acacia, dispersing, or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); polysaccharides and polysaccharide-like compounds (e.g., dextran sulfate); glycoaminoglycans and glycosaminoglycan-like compounds (e.g., hyaluronic acid); and thickening agents, such as carbomer, beeswax, hard paraffin, or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

Compositions can be designed to introduce the compounds to a desired site of action and release it at an appropriate and controllable rate. For example, controlled release preparations can be produced by the use of polymers to complex or absorb the compounds. A controlled-release formulation can be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers.

Alternatively, instead of incorporating these active ingredients into polymeric particles, it is possible to entrap these materials into microcapsules. Microencapsulation has been applied to the injection of microencapsulated pharmaceuticals to give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the compounds are all factors that must be considered. Examples of useful polymers are polycarbonates, polyesters, polyurethanes, polyorthoesters, and polyamides, particularly those that are biodegradable.

Microcapsules can be prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nanoparticles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

A frequent choice of a carrier for pharmaceuticals is poly (d,l-lactide-co-glycolide) (PLGA). This is a biodegradable polyester that has a long history of medical use in erodible sutures, bone plates, and other temporary prostheses where it has not exhibited any toxicity. A wide variety of pharmaceuticals, including peptides and antigens, have been formulated into PLGA microcapsules. A body of data has accumulated on the adaption of PLGA for the controlled release of compounds, for example, as reviewed by Eldridge, J. H., et al., Current Topics in Microbiology and Immunology. 1989, 146:59-66. The entrapment of compounds in PLGA microspheres of 1 to 10 microns in diameter has been shown to have a remarkable adjuvant effect when administered orally. The PLGA microencapsulation process uses a phase separation of a water-in-oil emulsion. The compound of interest is prepared as an aqueous solution and the PLGA is dissolved in suitable organic solvents such as methylene chloride and ethyl acetate. These two immiscible solutions are co-emulsified by high-speed stirring. A non-solvent for the polymer is then added, causing precipitation of the polymer around the aqueous droplets to form embryonic microcapsules. The microcapsules are collected and stabilized with one of an assortment of agents (polyvinyl alcohol (PVA), gelatin, alginates, polyvinylpyrrolidone (PVP), methyl cellulose), and the solvent removed by either drying in vacuo or by solvent extraction.

The pharmaceutical compositions may also be in the form of oil-in water emulsions. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri(caprylate/caprate) or propylene glycol dioleate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant can be a mixture of emulsifier(s), micelle-forming agent, and oil such as that which is commercially available under the name Provax® (IDEC Pharmaceuticals, San Diego, Calif.). The emulsion may also contain sweetening and flavoring agents. Syrups and elixirs may be formulated with sweetening agents, such as glycerol, sorbitol, or sucrose. Such formulations may also contain a demulcent, a preservative, a flavoring, or a coloring agent.

Additionally, the pharmaceutical compositions may be in the form of a sterile injectable preparation, such as a sterile injectable aqueous emulsion or oleaginous suspension. This emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propane-diol.

The sterile injectable preparation may also be prepared as a lyophilized powder. Among the acceptable vehicles and solvents that may be employed are water, Ringer's solution, and an isotonic sodium chloride solution. In addition, sterile fixed oils may be employed as a solvent or suspending medium. For this purpose, any bland fixed oil may be employed including synthetic mono- or diglycerides. In addition, fatty acids such as oleic acid may be used in the preparation of injectables.

In some embodiments, cyclodextrins may be added as aqueous solubility enhancers. Preferred cyclodextrins include hydroxypropyl, hydroxyethyl, glucosyl, maltosyl and maltotriosyl derivatives of cyclodextrin. An exemplary cyclodextrin solubility enhancer is hydroxypropyl-o-cyclodextrin (BPBC), which may be added to any of the above-described compositions to further improve the aqueous solubility characteristics of the compounds of the embodiments. In one embodiment, the composition comprises about 0.1% to about 20% hydroxypropyl-o-cyclodextrin, more preferably about 1% to about 15% hydroxypropyl-o-cyclodextrin, and even more preferably from about 2.5% to about 10% hydroxypropyl-o-cyclodextrin. The amount of solubility enhancer employed will depend on the amount of the compound of the embodiments in the composition.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, but are not limited to, mineral salts (e.g., $AlK(SO_4)_2$, $AlNa(SO_4)_2$, $AlNH(SO_4)_2$, silica, alum, $Al(OH)_3$, $Ca_3(PO_4)_2$, kaolin, or carbon).

In general, pharmaceutical compositions are prepared by uniformly and intimately associating the active ingredient with liquid carriers or finely divided solid carriers or both, and then, if necessary, shaping the product. For example, a tablet may be made by compression or molding. Compressed tablets may be prepared by compressing, in a suitable machine, an active ingredient in a free-flowing form such as a powder or granules, optionally mixed with a binder, lubricant, inert diluent, preservative, surface-active or dispersing agent. Molded tablets may be produced by molding, in a suitable apparatus, a mixture of powdered compound moistened with an inert liquid diluent. The tablets may optionally be coated or scored and may be formulated so as to provide a slow or controlled release of the active ingredient therein.

Compounds including disclosed pharmaceutical compositions can be packaged in unit dosage forms for ease of administration and uniformity of dosage. A "unit dosage form" as used herein refers to a physically discrete unit suited as unitary dosages for the subject to be treated; each unit containing a predetermined quantity of compound optionally in association with a pharmaceutical carrier (e.g., excipient, diluent, vehicle or filling agent) which, when administered in one or more doses, is calculated to produce a desired effect (e.g., prophylactic or therapeutic effect or benefit). Unit dosage forms can contain a weekly or monthly dose, or an appropriate fraction thereof, of an administered compound. Unit dosage forms also include, for example, capsules, troches, cachets, lozenges, tablets, ampules, and vials, which may include a composition in a freeze-dried or lyophilized state; a sterile liquid carrier, for example, can be added prior to administration or delivery in vivo. Unit dosage forms additionally include, for example, ampules and vials with liquid compositions disposed therein. The individual unit dosage forms can be included in multi-dose kits or containers. Pharmaceutical formulations can be packaged in single or multiple unit dosage forms for ease of administration and uniformity of dosage.

The compositions disclosed herein can be administered in accordance with the methods at any frequency and as a single bolus or multiple doses, for as long as appropriate. Exemplary frequencies are typically from 1-5 times, 1-3 times, 2-times, or once monthly. In some embodiments, the compounds will be administered for a period of continuous therapy, for example for a week or more, or for months or years. Long-acting pharmaceutical compositions may be administered twice a week, every 3 to 4 days, or every week depending on half-life and clearance rate of the particular formulation.

EXAMPLES

Example 1: Conflict Model of Anxiolysis

The conflict procedure methodology includes a two-component multiple fixed-ratio, fixed-ratio plus punishment schedule (mult FR, FR+PUN). An important feature of this model is that it is highly predictive of clinically active doses in human subjects (Rowlett et al. 2006, *Psychopharmacology* 184: 201-11). One component of this schedule was associated with a distinctive visual stimulus (e.g., red light) and the other component was associated with a different stimulus (e.g., green light). In each component, completion of 10 responses (FR 10) produced a food pellet followed by a brief (10 sec) timeout period. The component ended following delivery of 5 food pellets or 5 min, whichever occurred first. A 10-min timeout period occurred before each of four cycles with two components (1 red, 1 green) per cycle. When performance in both components of the multiple schedule was stable, responding in one component was suppressed by superimposing a FR schedule of response-produced electric shock. Under the superimposed schedule, every nth response (n=15-25, adjusted for each monkey depending on individual performance) produced shock. Once responding was stable (at least three sessions in which suppressed responding was less than 50% of non-suppressed responding, with no upward or downward trend in response rates in either component), investigational compounds were administered i.v. during the extended timeout periods using a cumulative dosing technique. This technique allowed determination of a four-point dose-response function in a single session.

Table 2 summarizes data for TPA023B in the conflict procedure (n=4 monkeys, 2 females and 2 males), with alprazolam as a positive control. Average responses when vehicle was administered was 2.2 in the non-suppressed component, decreased by ~98% by shock presentation in the suppressed component (mean=0.05 responses). For non-suppressed responding, TPA023B had no effects on mean rates of responding or percent of control over a 100-fold dose range (0.01 to 1.0 mg/kg, i.v.). The comparator drug, alprazolam, markedly attenuated non-suppressed responding at a dose of 0.3 mg/kg, i.v. For suppressed responding, TPA023B significantly enhanced rates of suppressed responding, reaching non-suppressed levels of responding at 0.1 mg/kg, i.v., i.e., this compound showed an anti-conflict effect. This effect was similar to that observed with 0.03 mg/kg, i.v., of alprazolam. A striking characteristic of TPA023B in this procedure is the lack of attenuation of rates of responding at higher doses. In contrast, rate-suppressing effects are shown here with alprazolam and demonstrated with a series of other conventional benzodiazepines (Rowlett et al. 2006).

TABLE 2

Effects of TPA023B on suppressed and non-suppressed responding in a rhesus monkey conflict procedure.

| Treatment(mg/kg, i.v.) | Non-Suppressed | Suppressed |
|---|---|---|
| | Mean responses/s (SEM) | |
| Vehicle | 2.2 (0.16) | 0.05 (0.01) |
| 0.01 | 2.0 (0.08) | 0.03 (0.02) |
| 0.1 | 2.0 (0.15) | 2.46 (0.40)* |
| 1.0 | 2.1 (0.97) | 2.00 (0.75)* |
| Alprazolam (0.03) | 1.8 (0.31) | 1.9 (0.10)* |
| Alprazolam (0.3) | 0.18 (0.09)* | 0.10 (0.10) |
| | % Non-Suppressed Vehicle (SEM) | |
| Vehicle | 100 (7.5) | 2.4 (0.13) |
| 0.01 | 95 (3.7) | 1.4 (0.82) |
| 0.1 | 95 (7.2) | 112 (16)* |
| 1.0 | 96 (46) | 91 (37)* |
| Alprazolam (0.03) | 82 (18) | 86 (4.5)* |
| Alprazolam (0.3) | 8.2 (4.0)* | 4.5 (4.5) |

*$P < 0.05$ vs. corresponding vehicle control, Bonferroni t-tests;
N = 4 monkeys In summary, TPA023B demonstrated anti-conflict effects to a degree associated with conventional anxiolytic benzodiazepines, but unlike benzodiazepines, it showed no propensity to impair the subjects' ability to complete responses, i.e., to induce motor coordination deficits.

Example 2: Observation/Sedation

For the data shown here, the behavior of each monkey (n=4 total) was scored using a focal animal approach as described previously (Duke et al. 2018, *J Pharmacol Exp Ther* 366: 145-57). Briefly, a trained observer blind to the drug treatments observed a specific monkey for 5 min and recorded each instance that a particular behavior occurred during 15-s intervals. Scores for each behavior were calculated as the number of 15-s bins in which the behavior occurred (e.g., a maximum score would be 20). For sedation measures, structured exposure to stimuli were included in the observation sessions (Duke et al., 2018). When a monkey was observed to have closed eyes for more than 3 s, an assessment of the animal's responsiveness to the stimuli was determined. Specifically, the observer presented three stimuli: 1) walked at a normal pace towards the cage, 2) spoke the animal's name, and 3) moved the lock used to secure the door of the cage. If the monkey responded immediately (i.e., opened eyes and oriented to the observer), "rest/sleep posture" was scored. If the monkey attended more slowly (i.e., >3 s following stimuli), the observer scored "moderate sedation". If the monkey did not open eyes across/throughout the 15-s interval after all three stimuli, the observer noted the loss of ability to respond to external stimuli and made as assessment of "deep sedation".

When scoring moderate or deep sedation, the monkey might be observed to be assuming an atypical posture that differed from the characteristic rest/sleep posture (e.g., unable to keep an upright posture). The assessment of sedation was initiated during the 5-min sampling period if the animal presented, at any time during that period, with its eyes closed for longer than 3 s. The result of this assessment was recorded for each remaining 15-sec interval of the 60-sec epoch unless eyes opened. Afterwards, eyes closing again initiated the assessment. If eyes remained closed, then the assessment was repeated at the beginning of the next 60-sec epoch 15-sec interval. Therefore, the maximum score for sedation during a 5-min period was 20 (four possible scores for 4×15-sec intervals per min, 5 min total; i.e., 4 possible scores×5 min=20). The order in which animals were observed and the observer performing the scoring each day was randomized. Four observers participated in the scoring throughout the duration of the study; each observer underwent a minimum of 20 hours of training and met an inter-observer reliability criterion of ≥90% agreement with all other observers.

The five-min sampling periods were repeated at multiple times following i.v. injection of TPA023B or vehicle (minutes post injection): 5, 10, 20, 40, 80, 160, 320. Scores were cumulated across the time periods, resulting in a maximum possible cumulative score of 140. TPA023B was compared with alprazolam, and the results have been published by Duke et al. (2018). The key results are summarized in Table 3. Notably, however, Duke et al. 2018 did not discuss the potential use of TPA023B as a treatment for benzodiazepine misuse and/or use disorder.

TABLE 3

Summary of significant behavioral effects (out of 22 total) following multiple doses of alprazolam and TPA023B. Significant effects were identified as at least one dose significantly different from vehicle (N = 4 monkeys).

| Compounds | Increase | Decrease |
| --- | --- | --- |
| Alprazolam | Rest/Sleep Posture, Moderate Sedation, Deep Sedation, Observable Ataxia | Passive Visual, Tactile/Oral Exploration |
| TPA023B | Rest/Sleep Posture | Tactile/Oral Exploration |

See above for definitions of Rest/Sleep Posture, Moderate and Deep Sedation.
For other definitions:
Observable ataxia - any slip, trip, fall, loss of balance; Passive
Visual - animal is standing or sitting motionless with eyes open; Tactile/Oral
Exploration - any tactile or oral manipulation of the cage or environment.

Consistent with findings from studies with human patients (Atack et al. 2010), TPA023B was well-tolerated by rhesus monkeys up to doses of 1.0 mg/kg, i.v. (30-fold higher than the lowest dose inducing rest/sleep posture). At doses of 0.03 to 1.0 mg/kg, i.v., TPA023B induced rest/sleep posture that corresponds to a mild form of sedation in which the subject can be roused easily by stimuli.

Example 3: Self-Administration

The abuse potential of novel compounds can be determined by use of i.v. self-administration procedures, in which a compound is available to a subject previously trained to press a lever to obtain a known drug of abuse. Our standard procedure is to use a progressive-ratio (PR) schedule, in which an increasing number of responses are required to obtain an injection. The last response requirement completed is referred to as a "break point" (BP) and represents the maximum amount of "work" a subject will perform to obtain the drug or compound.

In the present example, eight rhesus monkeys (4 females, 4 males) were trained to respond under a schedule of i.v. midazolam (a conventional benzodiazepine) injection at 0.03 mg/kg/injection. Once self-administration had been acquired (>20 injections/daily 2-hour sessions), monkeys were trained under the PR schedule as described by Shinday et al. (2013). Daily experimental sessions consisted of five components, each made up of four trials (i.e., 20 trials total). Each trial within a component had the same response requirement and was separated by a timeout (30 min of no lights or lever availability) in order to minimize drug accumulation due to repeated injections in a single session. A session ended when the response requirement was not met within a 30-min limited hold for two consecutive trials or when all 20 trials are completed. The PR sequence had an initial response requirement of 40 per injection and doubled at the start of each component (i.e., response requirements of 40, 80, 160, 320, 640). Training sessions alternated with drug and saline according to the following 5-session cycles: DSSDD, SDDSS (S=saline or D=drug). Responding under the PR schedule was considered stable across the cycles when the number of injections/session were less than 5 for at least three sessions of saline availability and greater than 11 for at least three sessions of drug availability, with no consistent upward or downward trends. Test sessions were inserted into the sequence every third session, e.g., DST-SDTD, STDDTSS, and so on (T=test). Test conditions included TPA023B, in comparison with the conventional benzodiazepine lorazepam, which has a similar duration of action to the test compound.

A range of doses for lorazepam (0.001-0.03 mg/kg/injection) and TPA023B (0.003-0.03 mg/kg/injection) was tested and for both, 2+ doses maintained a significantly higher level of mean number of injections/session than maintained by vehicle alone (vehicle generally resulted in 3-4 injections/session, since no cues signaled drug availability). In order to directly compare lorazepam and TPA023B self-administration, we here analyzed BP values at the doses that maintained the highest level of mean injections/session and compared these BP values with those obtained after vehicle tests.

Figure 5:
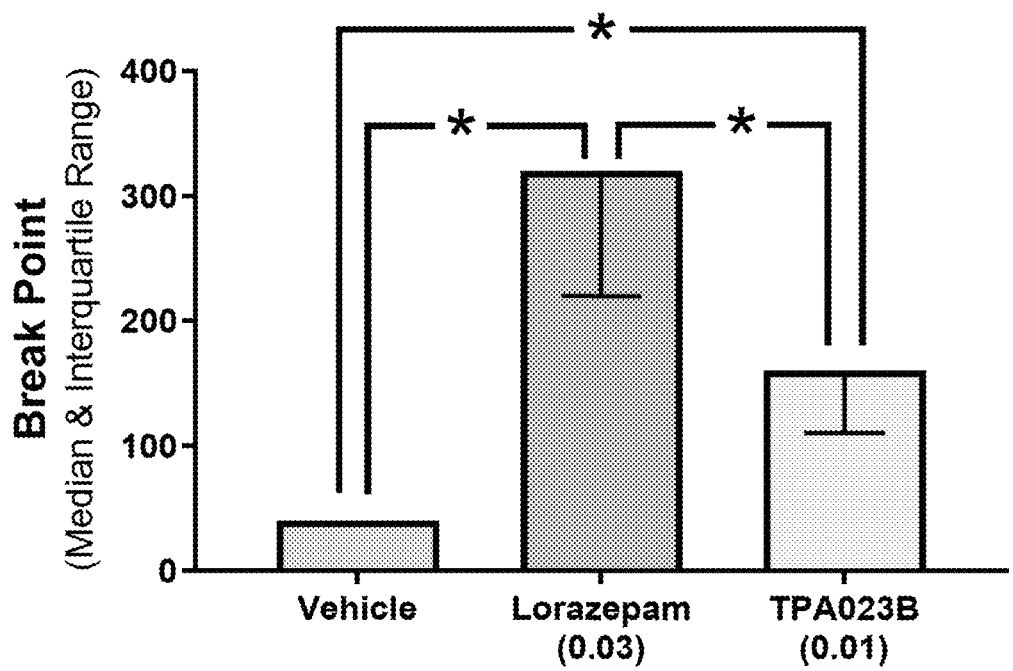
FIG. 5 illustrates break points (highest response requirement obtained) for maximally self-administered doses of lorazepam and TPA023B (doses are in parenthesis on x-axis, in mg/kg/injection). These values were compared with break points obtained when vehicle was available. Data are median and interquartile ranges for n=4 monkeys and were analyzed with Friedman's repeated measures ANOVA on ranks. Note that *p<0.05, Dunnett's tests for ranks.

As can be seen in FIG. 5, lorazepam at the dose in which self-administration was highest resulted in a median BP of 320, whereas the highest response requirement maintained by TPA023B was 160. These values were significantly different (Dunnett's test for ranks, $p<0.05$). Both lorazepam and TPA023B, as expected, maintained median BP values significantly higher than those maintained by vehicle (Dunnett's tests for ranks, $p<0.05$). These findings suggest that while TPA023B was a reinforcer, it had significantly lower reinforcing effectiveness than the conventional benzodiazepine lorazepam. These findings are consistent with TPA023B being predominantly a partial positive modulator/antagonist at $GABA_A$ receptor subtypes.

Example 4: Specific Suppression of Self-Administration of Benzodiazepines

TPA023B showed anti-conflict effects, consistent with this compound having anxiolytic-like effects, similar to conventional benzodiazepines. When sedative-motor effects were compared with the conventional benzodiazepine alprazolam (Xanax®), TPA023B showed only mild sedation and no motor deficits. And when evaluated for abuse potential, TPA023B demonstrated a lower potential for abuse than lorazepam (Ativan®), which is self-administered to the same degree as all conventional benzodiazepines in our PR procedure. A key question for evaluation of this compound as a potential pharmacotherapy is the extent to which it attenuates the reinforcing effects of a conventional benzodiazepine, under conditions in which TPA023B is a weak reinforcer.

To test this, we have trained monkeys to self-administer the short-acting conventional benzodiazepine midazolam (0.056 mg/kg/injection, i.v.) in the PR procedure, as described above. During test sessions, we initially kept the training dose of midazolam constant, and administered i.v. pretreatments of TPA023B (0.003, 0.01, 0.03, 0.1, 0.3 mg/kg, of vehicle) immediately prior to the beginning of the session. A key consideration for any pharmacotherapy, as well as interpretation of blockade of reinforcing effects generally, is the extent to which the blockade is specific to the drug target and not a generalized suppression of behavior, e.g., due to sedative-motor effects inhibiting the ability of the monkey to press the lever. Another possible confounding factor that would potentially result in blockade of drug taking is general sickness or perceptual alterations. In particular, appetite suppression would represent an undesirable side effect in a benzodiazepine addiction pharmacotherapy. To evaluate the extent to which suppression of lever-pressing behavior by TPA023B represents non-specific inhibition, we also tested food self-administration under the PR schedule. For these experiments, test sessions were scheduled similar to those with midazolam dose/vehicle, except that 2 food pellets (1-g BioServ flavored food pellets) were available as reinforcers rather than midazolam dose. All other aspects of the test was the same, including response requirements and TPA023B pretreatment conditions.

Figure 6:
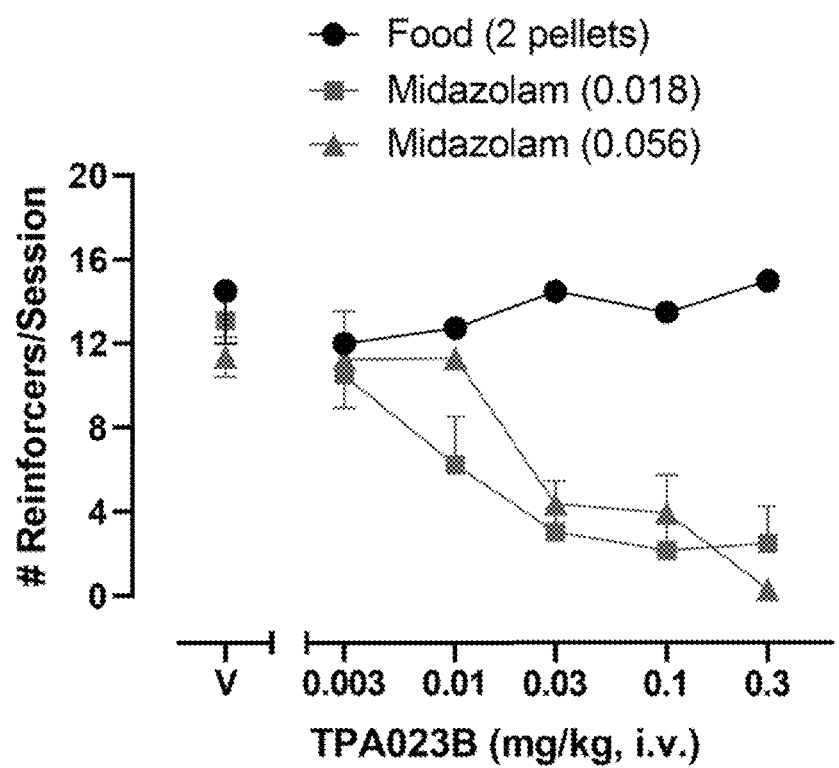
FIG. 6 illustrates self-administration of midazolam (MZ, 0.018 and 0.056 mg/kg/injection) and food (2 pellets/delivery) under a PR schedule, following TPA023B pretreatments. Data are mean number of reinforcers, +/−SEM, with a "Reinforcer" consisting of an injection of midazolam or delivery of 2 pellets. V, midazolam vehicle. N=4 monkeys.

FIG. 6 shows the effects of pretreatments with TPA023B on self-administration of two doses of midazolam and food pellets in four rhesus monkeys. Points above "V" (vehicle) show that both midazolam and food pellet delivery maintained between 11 and 15 reinforcers per session out of 20 possible, which was essentially the same as baseline responding. Increasing doses of TPA023B reduced midazolam-maintained responding at both doses, with a >50% reduction at 0.03 mg/kg. In contrast, TPA023B did not alter food-maintained responding up to 0.3 mg/kg. These findings clearly show that TPA023B blocks the self-administration of the benzodiazepine midazolam without altering food self-administration, showing the desired specificity and suggesting that the suppression of responding is not due to sedative-motor effects and/or attenuation of general reinforcing processes.

Example 5: Dosage Evaluation for Benzodiazepine Suppression & Anxiolysis Effects To further evaluate the extent to which attenuation of responding was due to pharmacological antagonism and to evaluate an exemplary range of effective doses, we evaluated single doses of TPA023B administered prior to sessions in which differing doses of midazolam were tested.

Figure 7A:
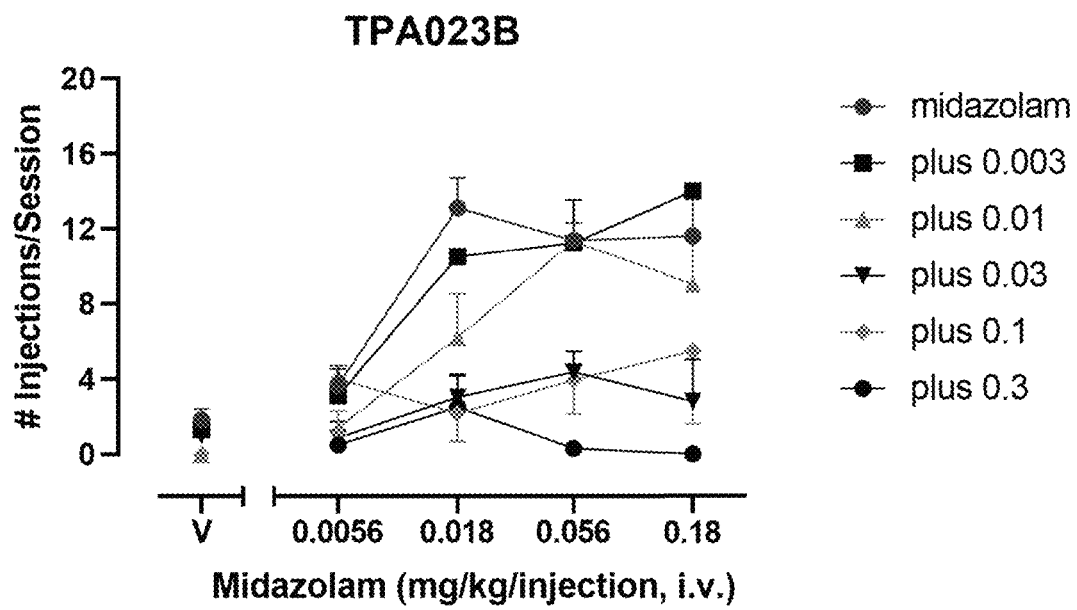
FIGS. 7A and 7B illustrate dose-response function for midazolam self-administration in the PR procedure (N=4 monkeys).
Figure 7B:
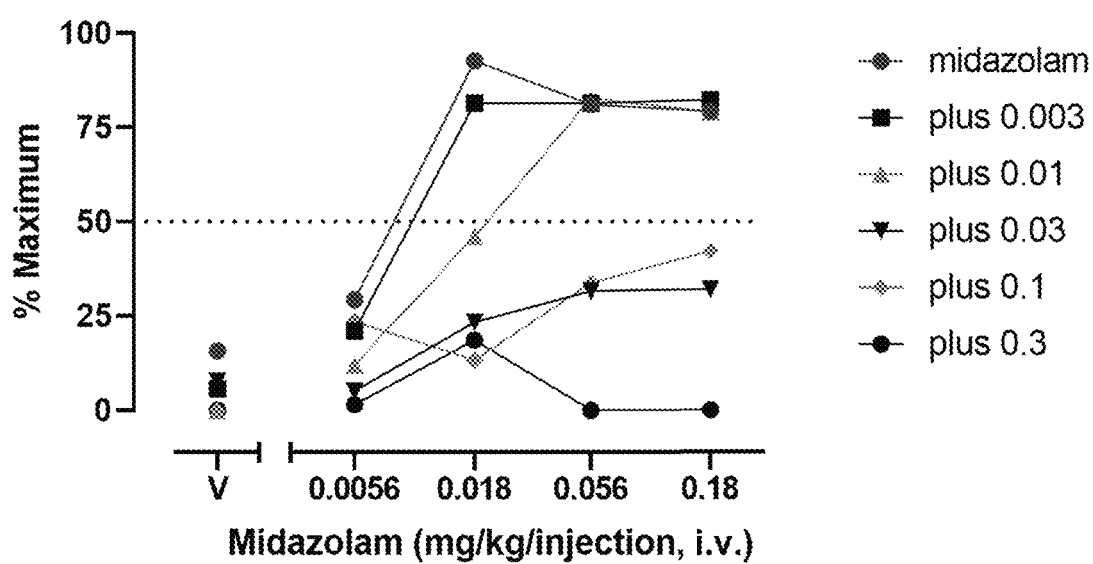

FIGS. 7A and 7B show both raw data (FIG. 7A, number of injections/session) and percent maximum (FIG. 7B, % of each monkey's maximum number of injections/session). The Figures demonstrate that midazolam alone resulted in dose-dependent self-administration of 0.018, 0.056, and 0.18 mg/kg/injection, but not 0.0056 mg/kg/injection, with the 0.018 mg/kg/injection dose showing maximal self-administration. Pretreatment with 0.003 mg/kg TPA023B did not attenuate self-administration of midazolam but increasing the TPA023B dose to 0.01 mg/kg shifted the midazolam dose-response function to the right. That is, TPA023B suppressed self-administration of midazolam at 0.018 mg/kg/injection but when the midazolam dose was increased, responding returned to maximal levels (see FIG. 4, bottom panel).

At higher doses of TPA023B, the midazolam dose-response function was shifted to the right and down, with self-administration generally not reaching 50% of maximum, even at the relatively higher midazolam doses. In other words, the suppression of midazolam self-administration by TPA023B was not fully surmountable, meaning that re-establishing midazolam taking cannot occur simply by taking higher doses of the benzodiazepine. These data further support TPA023B's ability to block the effects of a conventional benzodiazepine irrespective of sedative and/or motor effects and demonstrate a surprising insurmountable profile.

Figure 8:
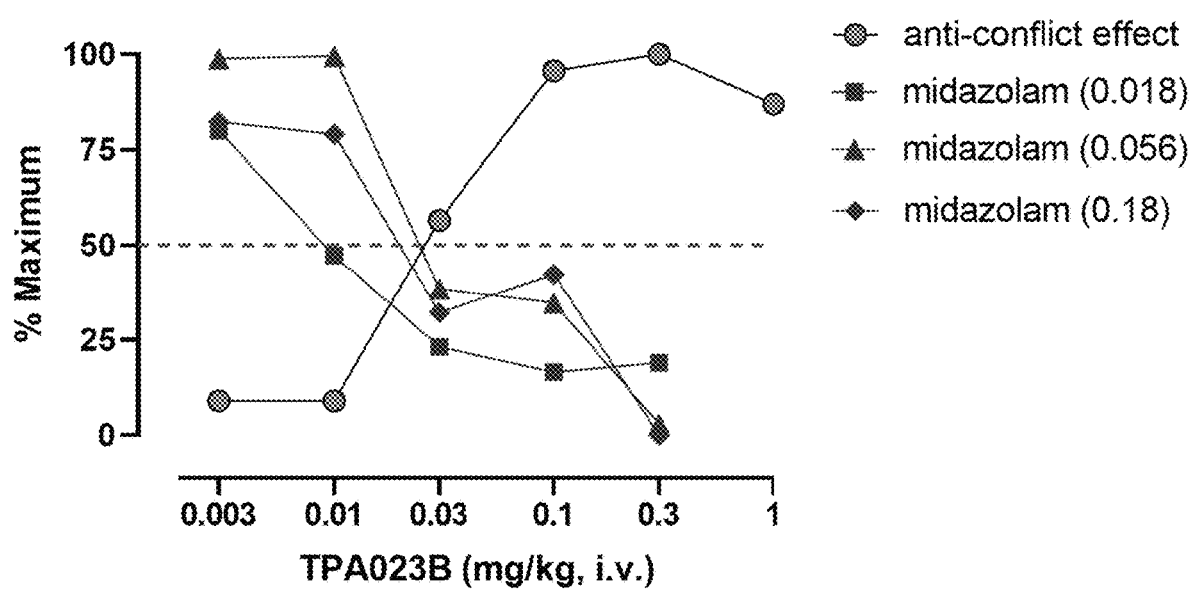
FIG. 8 illustrates a comparison of TPA023B anti-conflict effects and blockade of midazolam self-administration in rhesus monkeys. Data are percent maximal effects for individual monkeys, averaged together. N=8 (4 for conflict, 4 for self-administration).

To illustrate the relationship of anxiolysis to blockade of benzodiazepine self-administration, FIG. 8 plots the highest three doses of midazolam self-administration along with the conflict data from Table 2 as average % maximum effect. When plotted as percent maximum, TPA023B increased suppressed responding ("anti-conflict effect") in a dose-dependent manner. As noted above, TPA023B dose-dependently reduced midazolam self-administration to below 50% for all midazolam doses, with attenuation consistently below 25% for the highest TPA023B dose. For both conflict and blockade of self-administration, TPA023B doses at and above 0.03 mg/kg had both anti-conflict effects and blocked midazolam self-administration. TPA023B thus attenuated the reinforcing effects of midazolam at the same doses that engendered an increase in anxiolytic-like effects, suggesting that TPA023B retains anxiolysis with the ability to block benzodiazepine self-administration.

Example 6: Evaluation of Respiratory Depression

Although considered safe relative to several other drugs in psychiatric medicine, benzodiazepines are known respiratory depressants. The effects of benzodiazepines on pulmonary ventilation are considered modest; however they do represent risk for aspiration and their use is contraindicated with sleep apnea. Importantly, increased risk of overdose death occurs when benzodiazepines are combined with alcohol and/or opioids. Therefore, we have initiated studies to assess potential respiratory depressant effects of our partial positive modulators.

We first assessed the effects of TPA023B, in comparison with alprazolam, using whole body plethysmography (WBP; DSI systems). For these studies, adult male Sprague-Dawley rats (n=8) were habituated to the chambers for 30 min. The chamber was then filled with 21% oxygen, sealed, and pressure fluctuation measured for 1 min. Next, the chamber was opened and the rats were injected with alprazolam or TPA023B, i.p., and placed into the sealed chamber for a 15 min pretreatment time. The chamber was again filled with 21% oxygen, and for 1 min, fluctuating pressure amounts were recorded to obtain tidal volume (lung capacity), breaths/minute, and minute volume (lung capacity per unit time).

Figure 9:
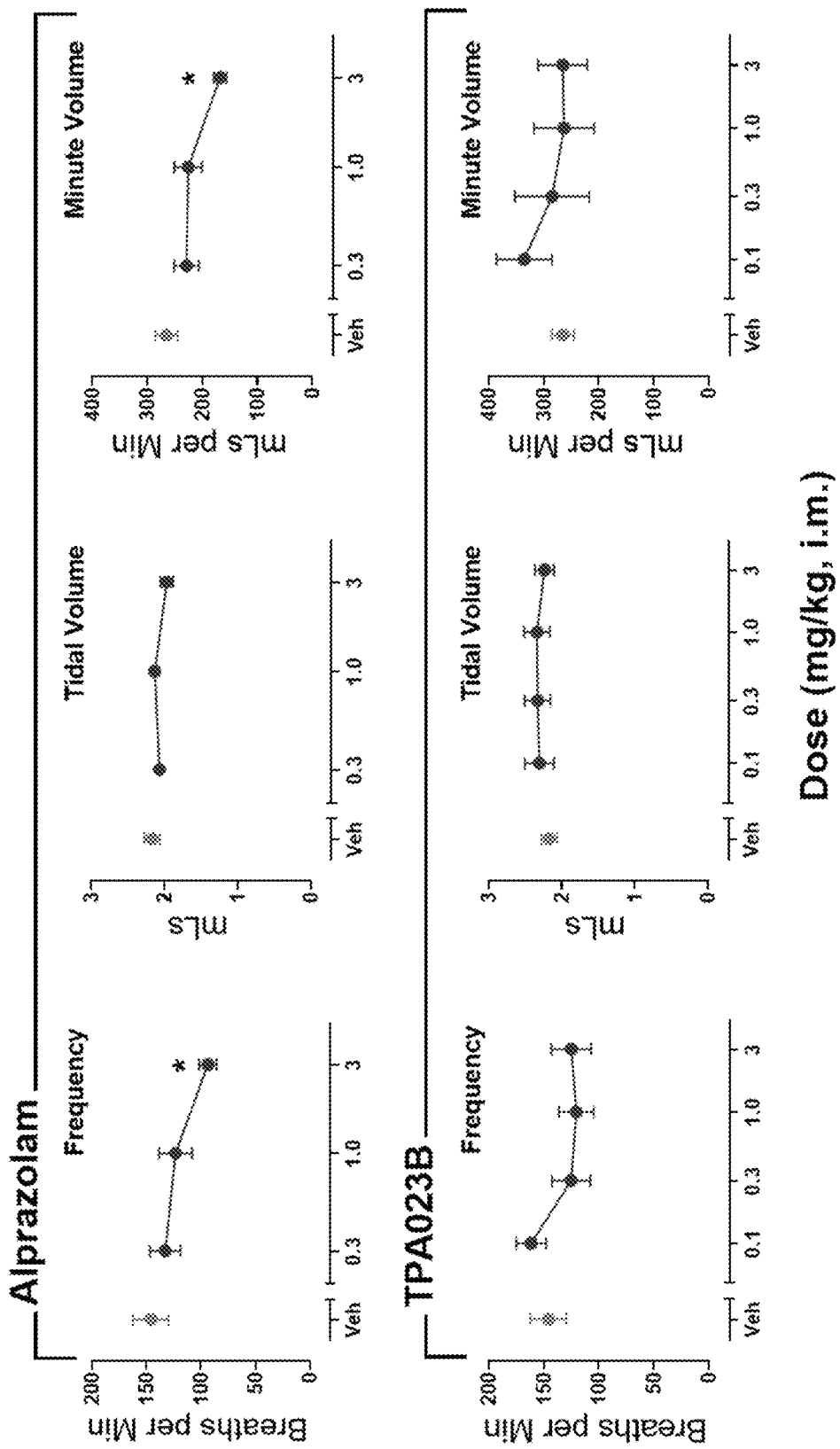
FIG. 9 illustrates pulmonary ventilation following alprazolam and TPA023B administration in adult male Sprague-Dawley rats (N=8). Respiration parameters were measured via whole body plethysmography and presented as mean+/−SEM for each measure. Note that *p<0.05 vs. vehicle treatment ("Veh"), Bonferroni t-tests. TPA023B had no effects on any respiratory measure, either by ANOVA or Bonferroni t-tests.

FIG. 9 shows results from testing with alprazolam and TPA023B in 8 rats, tested once or twice per week. Alprazolam significantly reduced breathing frequency and minute volume at 3.0 mg/kg, but not tidal volume. In contrast, TPA023B did not alter any ventilatory parameter over the doses tested. Importantly, the doses were chosen as those that occupied up to 95% of benzodiazepine binding sites (1.0 and 3.0 mg/kg, Atack et al. 2010). These findings demonstrate low toxicity for partial positive modulators, a key property given that benzodiazepine addiction patients are likely to abuse other substances as well.

Example 7: Evaluation of Physical Dependence & Withdrawal

A well-documented consequence of benzodiazepine exposure, and important contributor to the abuse of these drugs, is physical dependence (Licata & Rowlett 2008, *Pharmacol Biochem Behav* 90: 74-89). Physical dependence occurs when exposure to a drug leads to aversive, or even life-threatening, consequences upon cessation of the drug exposure. Cessation can result either by "spontaneous withdrawal" (abrupt removal of drug treatment) or precipitated withdrawal (administration of a drug with antagonist properties). Benzodiazepine withdrawal signs include gastrointestinal disturbances (e.g., nausea, vomiting), anxiety, sleeplessness, tremors, and in severe cases, seizures. Alleviation of withdrawal may be a major factor contributing to relapse to benzodiazepine taking.

Mild withdrawal syndromes can occur even after a single, relatively large bolus exposure to a benzodiazepine. This effect may be an earlier contributor to benzodiazepine addiction, particularly in vulnerable patients (e.g., induction of mild anxiety conceivably could drive an anxiety patient to seek additional benzodiazepines). Acute dependence can be demonstrated in non-human animals, providing a means to study early events in the addiction cycle but also providing an approach that reduces risk to the subjects.

Acute dependence can occur after single exposures to the benzodiazepine chlordiazepoxide, but not to an $\alpha 2/3GABA_A$ selective ligand (Fischer et al. 2013, *Psychopharmacology* 227: 347-54). Here, the extent to which TPA023B can precipitate withdrawal in rats following a single, large bolus dose of diazepam was studied. For these studies, adult Sprague-Dawley rats (N=8) were trained to press a lever 10 times to receive a food pellet (FR 10 schedule) during daily 10 minute sessions. Once rates of responding were stable, doses of diazepam, the non-selective benzodiazepine antagonist flumazenil, and TPA023B were administered prior to the session.

Figures 10A, 10B, 10C:
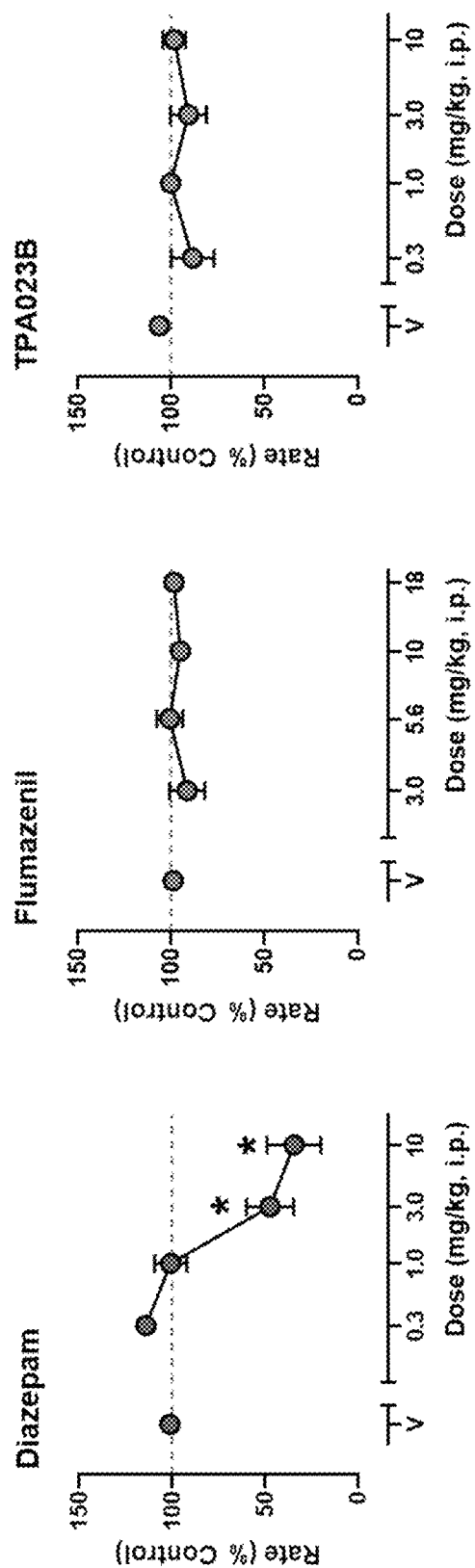
FIGS. 10A to 10C illustrate effects of the full modulator diazepam, the antagonist flumazenil, and the selective partial modulator TPA023B on rates of responding maintained by food in rats (N=8). Data are mean+/−percent of baseline responding prior to the test sessions. Note that *p<0.05, vs. vehicle (V), Bonferroni t-tests.

FIGS. 10A to 10C show that mean rates of responding (expressed as percent of baseline control) were significantly decreased by diazepam, but not flumazenil or TPA023B. We next varied the time between injection and testing for diazepam at 3.0 mg/kg, and found the most robust effects at 30 min pre-treatments before the session, and no effects at 60 min pre-treatment.

Figure 11A:
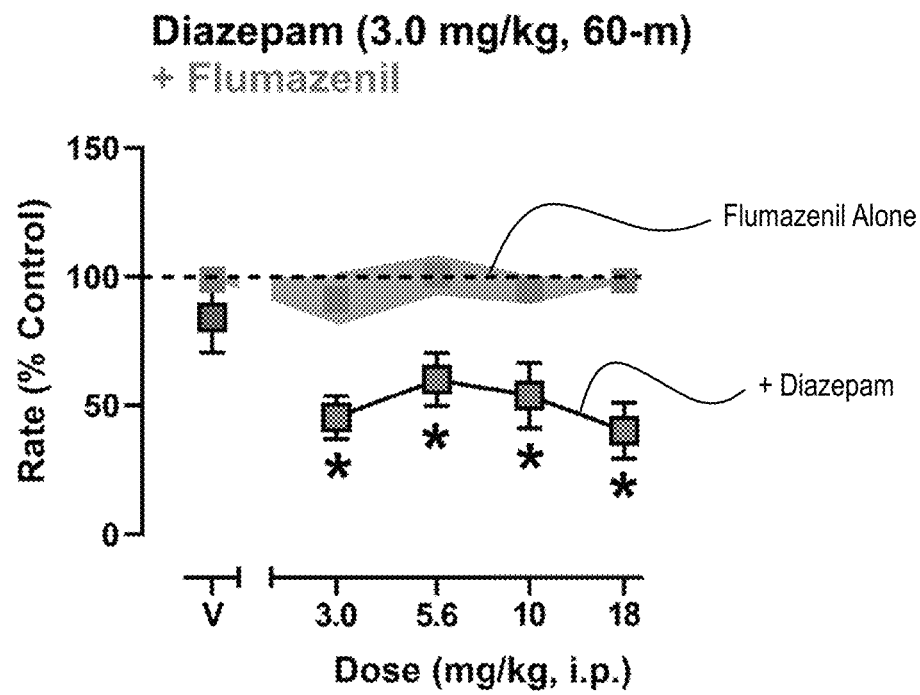
FIGS. 11A and 11B illustrate effects of flumazenil and TPA023B on rates of responding following 3.0 mg/kg of diazepam administered 60 min prior to the session. V, vehicle (i.e., diazepam alone). Note that *p<0.05 vs. ligand administered alone, Bonferroni t-tests.

To assess the extent to which flumazenil and TPA023B precipitate withdrawal, we evaluated the effects of pretreatments with both compounds prior to diazepam using the 60-min pre-treatment time, in which diazepam's effects had dissipated. As shown in FIG. 11A, re-testing the doses of flumazenil robustly suppressed responding at all doses tested compared with the rates after flumazenil alone. That is, flumazenil disrupted lever-pressing behavior 60 min after a bolus injection of diazepam, indicative of a withdrawal state.

Figure 11B:
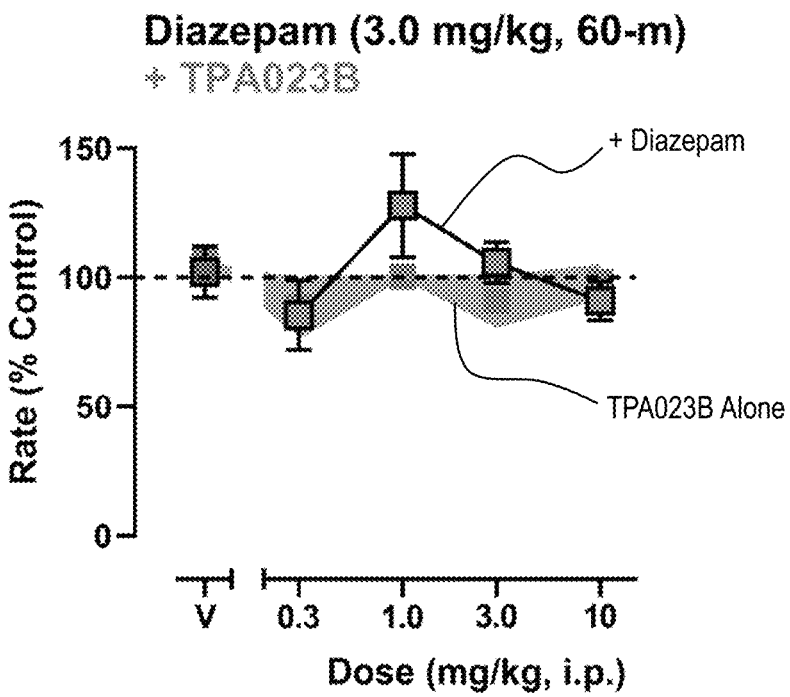

In contrast, as shown in FIG. 11B, TPA023B did not alter rates of responding at any dose tested (doses shown to occupy up to ~95% of benzodiazepine binding sites in brain (3.0 and 10 mg/kg)). These findings illustrate that TPA023B and similar compounds are not expected to precipitate withdrawal in dependent subjects, which would be a significant leap forward in treatment initiation, since patients with benzodiazepine addiction would not need to be detoxified from the benzodiazepine prior to therapy.

Example 8: Representative Imidazopyrimidine and Triazolopyridazine Compounds

TPA023B includes an imidazotriazine core. The compounds MRK-623 and L-838,417 were also evaluated as exemplary compounds with imidazopyrimidine and triazolopyridazine cores, respectively.

The triazolopyradizine L-838,417 has functional selectivity for $\alpha 2/3/5GABA_A$ receptors and is an $\alpha 1GABA_A$ antagonist. This profile is very similar to that of TPA023B despite the structural differences. The imidazopyrimidine, MRK-623, which has a different selectivity profile from TPA023B in that it is $\alpha 2/3GABA_A$ subtype selective. For both compounds, we chose 3.0 mg/kg, i.p., in rats based on published literature or pilot studies in our laboratories.

Figure 12A:
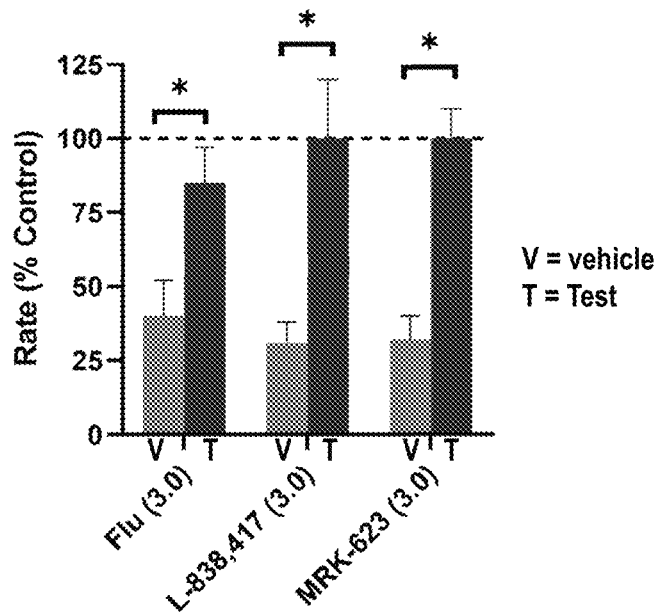
FIGS. 12A and 12B illustrate effects of the full modulator diazepam, the antagonist flumazenil (Flu), and the selective partial modulators L-838,417 and MRK-623 on rates of responding maintained by food in rats (N=5). Data are mean+/−percent of baseline responding prior to the test sessions. Note that *p<0.05, vs. vehicle (Veh), Bonferroni t-tests. "ns", non-significant.
Figure 12B:
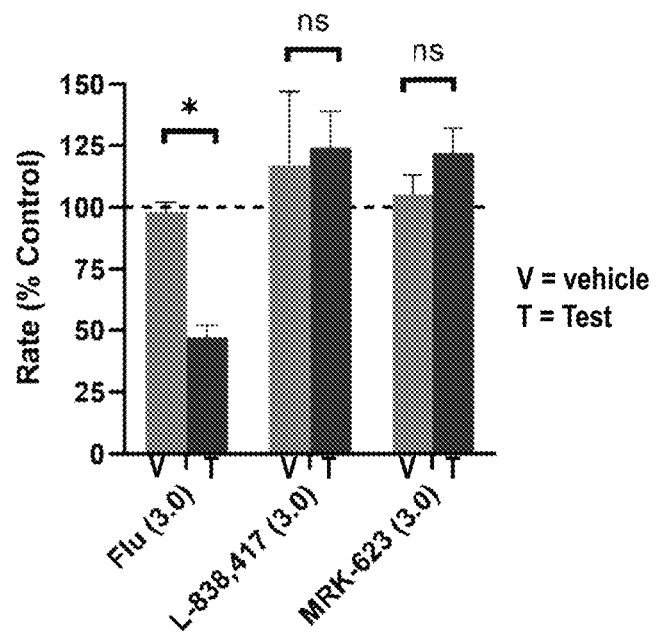

FIGS. 12A and 12B illustrate the results of acute dependency testing using these compounds. As shown, the dose of 3.0 mg/kg for the non-selective antagonist flumazenil, as well as L-838,417 and MRK-623, blocked the ability of diazepam (30 min pretreatment; FIG. 12A) to suppress rates of responding. When these same doses of the ligands were administered to rats after a 60-min pretreatment of diazepam (when diazepam's effects had dissipated; FIG. 12B), flumazenil induced a significant decrease in rates of responding, consistent with a withdrawal-like state and acute dependence. However, neither L-838,417 nor MRK-623 altered rates of responding, indicating that these compounds, like TPA023B, do not induce acute physical dependence.

Exemplary Embodiments

Embodiments of the present disclosure may include, but are not necessarily limited to, features recited in the following clauses:

Clause 1: A method of treating benzodiazepine misuse and/or use disorder, the method comprising administering to a subject in need thereof of an effective amount of a compound that provides both partial modulator and antagonist effects at $GABA_A$ receptors.

Clause 2: The method of Clause 1, wherein the compound is a compound of Formula I, Formula II, Formula III, or a combination or mixture thereof.

Clause 3: The method of any one of Clauses 1 to 2, wherein the compound provides an anxiolytic effect.

Clause 4: The method of Clause 3, wherein the anxiolytic effect is less than that from a benzodiazepine.

Clause 5: The method of any one of Clauses 1 to 4, wherein positive reinforcing effects of the compound are less than from a benzodiazepine.

Clause 6: The method of any one of Clauses 1 to 5, wherein the compound functions to suppress the effects of a benzodiazepine.

Clause 7: The method of Clause 6, wherein suppression is independent of sedative effects of the compound.

Clause 8: The method of Clause 6 or Clause 7, wherein the suppression is independent of motor effects of the compound.

Clause 9: The method of any one of Clauses 6 to 8, wherein the suppression is insurmountable and thus cannot be negated by increased benzodiazepine dosing.

Clause 10: The method of any one of Clauses 1 to 9, wherein the compound is administered at a dose of greater than or equal to about 0.01 mg/kg.

Clause 11: The method of any one of Clauses 1 to 9, wherein the compound is administered at a dose of greater than or equal to about 0.03 mg/kg.

Clause 12: The method of Clause 11, wherein the compound provides both anxiolytic and benzodiazepine suppression effects when administered.

Clause 13: The method of any one of Clauses 1 to 12, wherein the compound does not induce substantial motor coordination deficits in the subject.

Clause 14: The method of any one of Clauses 1 to 13, wherein the compound does not induce substantial appetite suppression in the subject.

Clause 15: The method of any one of Clauses 1 to 14, wherein the compound does not substantially affect breathing frequency, tidal volume, or minute volume in the subject.

Clause 16: The method of any one of Clauses 1 to 15, wherein the compound does not precipitate benzodiazepine withdrawal.

Clause 17: The method of any one of Clauses 1 to 16, wherein the compound is administered without prior or concurrent detoxification treatment of the subject.

Clause 18: The method of any one of Clauses 1 to 17, wherein the compound is partially or fully deuterated.

Clause 19: A compound for use in treating benzodiazepine misuse and/or use disorder according to a method as in any one of Clauses 1 to 18.

Additional Terms & Definitions

While certain embodiments of the present disclosure have been described in detail, with reference to specific configurations, parameters, components, elements, etcetera, the descriptions are illustrative and are not to be construed as limiting the scope of the claimed invention.

Furthermore, it should be understood that for any given element of component of a described embodiment, any of the possible alternatives listed for that element or component may generally be used individually or in combination with one another, unless implicitly or explicitly stated otherwise.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, less than 1%, less than 0.1%, or less than 0.01% of the stated amount, value, or condition. At the very least, and not as an attempt to limit the application of the doctrine of equivalents to the scope of the claims, each numerical parameter should be construed in light of the number of reported significant digits and by applying ordinary rounding techniques.

Any headings and subheadings used herein are for organizational purposes only and are not meant to be used to limit the scope of the description or the claims.

It will also be noted that, as used in this specification and the appended claims, the singular forms "a," "an" and "the" do not exclude plural referents unless the context clearly dictates otherwise. Thus, for example, an embodiment referencing a singular referent (e.g., "widget") may also include two or more such referents.

It will also be appreciated that embodiments described herein may also include properties and/or features (e.g., ingredients, components, members, elements, parts, and/or portions) described in one or more separate embodiments and are not necessarily limited strictly to the features expressly described for that particular embodiment. Accordingly, the various features of a given embodiment can be combined with and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include such features.

The invention claimed is:

1. A method of treating benzodiazepine misuse and/or use disorder, the method comprising:

identifying a subject as having benzodiazepine misuse and/or use disorder; and administering to the subject an effective amount of a compound providing partial modulatory effects for α2 and α3 $GABA_A$ receptor subtypes, the compound comprising the structure:

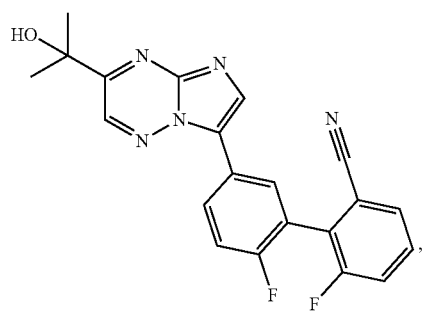 [SMILES: CC(C)(O)c1cnn2c(-c3ccc(F)c(-c4c(F)cccc4C#N)c3)cnc2n1]

wherein the compound is administered at a dose of greater than or equal to about 0.03 mg/kg wherein administration of the compound suppresses benzodiazepine self-administration, wherein the suppression is insurmountable and is not negated by increased benzodiazepine dosing, and wherein administration of the compound does not precipitate benzodiazepine withdrawal in the subject.

2. The method of claim 1, wherein the compound provides an anxiolytic effect less than that from a benzodiazepine.

3. The method of claim 1, wherein positive reinforcing effects of the compound are less than from a benzodiazepine.

4. The method of claim 1, wherein the compound functions to suppress the effects of a benzodiazepine independent of sedative or motor effects of the compound.

5. The method of claim 1, wherein the compound does not induce substantial motor coordination deficits.

6. The method of claim 1, wherein the compound provides both anxiolytic and suppression effects.

7. The method of claim 1, wherein the compound does not induce substantial appetite suppression in the subject.

8. The method of claim 1, wherein the compound does not substantially affect breathing frequency in the subject.

9. The method of claim 1, wherein the compound does not substantially affect tidal volume in the subject.

10. The method of claim 1, wherein the compound does not substantially affect minute volume in the subject.

11. A method of treating benzodiazepine misuse and/or use disorder, the method comprising:

identifying a subject as having benzodiazepine misuse and/or use disorder; and administering to the subject an effective amount of a compound providing partial modulatory effects for α2 and α3 GABA$_A$ receptor subtypes, the compound comprising the structure:

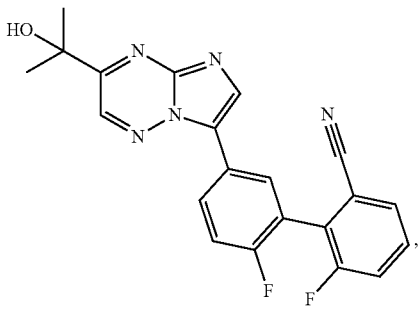 [SMILES: CC(C)(O)c1cnn2c(-c3ccc(F)c(-c4c(F)cccc4C#N)c3)cnc2n1]

wherein the compound is administered at a dose of greater than or equal to about 0.03 mg/kg wherein administration of the compound results in one or both of
 (i) the compound suppresses benzodiazepine self-administration, wherein the suppression is insurmountable and is not negated by increased benzodiazepine dosing,
 (ii) the compound does not precipitate benzodiazepine withdrawal in the subject.

12. The method of claim 11, wherein the compound provides an anxiolytic effect less than that from a benzodiazepine.

13. The method of claim 11, wherein positive reinforcing effects of the compound are less than from a benzodiazepine.

14. The method of claim 11, wherein the compound functions to suppress the effects of a benzodiazepine independent of sedative or motor effects of the compound.

15. The method of claim 11, wherein the compound provides anxiolytic effect.

16. The method of claim 11, wherein the compound does not induce substantial motor coordination deficits or appetite suppression in the subject, and does not substantially affect breathing frequency, tidal volume, or minute volume in the subject.

* * * * *